(12) United States Patent
Tomaschko et al.

(10) Patent No.: US 8,457,738 B2
(45) Date of Patent: Jun. 4, 2013

(54) PACING CATHETER FOR ACCESS TO MULTIPLE VESSELS

(75) Inventors: Daniel K. Tomaschko, Savage, MN (US); Richard J. Olson, Blaine, MN (US); Tracee Eidenschink, Wayzata, MN (US); Matthew C. Heidner, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 579 days.

(21) Appl. No.: 12/484,744

(22) Filed: Jun. 15, 2009

(65) Prior Publication Data

US 2009/0318991 A1    Dec. 24, 2009

Related U.S. Application Data

(60) Provisional application No. 61/074,035, filed on Jun. 19, 2008.

(51) Int. Cl.
*A61N 1/362* (2006.01)

(52) U.S. Cl.
USPC .......................................................... 607/10

(58) Field of Classification Search
USPC ............................................................ 607/9
See application file for complete search history.

(56) References Cited

U.S. PATENT DOCUMENTS

| | | |
|---|---|---|
| 3,769,984 A | 11/1973 | Muench |
| 3,837,347 A | 9/1974 | Tower |
| 3,865,118 A | 2/1975 | Bures |
| 3,893,461 A | 7/1975 | Preston |
| 3,915,174 A | 10/1975 | Preston |
| 3,942,536 A | 3/1976 | Mirowski et al. |
| 3,949,757 A | 4/1976 | Sabel |
| 4,030,508 A | 6/1977 | Thalen |
| 4,094,321 A | 6/1978 | Muto |
| 4,124,031 A | 11/1978 | Mensink et al. |
| 4,136,702 A | 1/1979 | Trabucco |
| 4,202,339 A | 5/1980 | Wirtzfeld et al. |
| 4,262,982 A | 4/1981 | Kenny |
| 4,365,639 A | 12/1982 | Goldreyer |
| 4,388,930 A | 6/1983 | De Bellis |
| 4,587,975 A | 5/1986 | Salo et al. |

(Continued)

FOREIGN PATENT DOCUMENTS

| | | |
|---|---|---|
| DE | 3300050 A1 | 7/1984 |
| EP | 2331194 B1 | 3/2012 |

(Continued)

OTHER PUBLICATIONS

"U.S. Appl. No. 11/113,828, Examiner Interview Summary mailed Feb. 4, 2011", 1 pg.

(Continued)

*Primary Examiner* — Eric D. Bertram
(74) *Attorney, Agent, or Firm* — Schwegman Lundberg & Woessner, P.A.

(57) ABSTRACT

Cardioprotective pacing is applied to prevent and/or reduce cardiac injury associated with myocardial infarction (MI) and revascularization procedure. Pacing pulses are generated from a pacemaker and delivered through a plurality of pacing leads introduced into a patient's body through a percutaneous transluminal vascular intervention (PTVI) catheter have a plurality of exit ports. In one embodiment, the exit ports are arranged for the pacing leads to enter multiple specified blood vessels.

20 Claims, 15 Drawing Sheets

U.S. PATENT DOCUMENTS

| | | | |
|---|---|---|---|
| 4,602,645 A * | 7/1986 | Barrington et al. | 607/123 |
| 4,702,253 A | 10/1987 | Nappholz et al. | |
| 4,763,655 A | 8/1988 | Wirtzfeld et al. | |
| 4,809,697 A | 3/1989 | Causey, III et al. | |
| 4,834,710 A | 5/1989 | Fleck | |
| 4,882,777 A | 11/1989 | Narula | |
| 4,919,133 A | 4/1990 | Chiang | |
| 4,955,382 A | 9/1990 | Franz et al. | |
| 4,962,767 A | 10/1990 | Brownlee | |
| 5,007,427 A | 4/1991 | Suzuki et al. | |
| 5,025,786 A | 6/1991 | Siegel | |
| 5,072,458 A | 12/1991 | Suzuki | |
| 5,099,839 A | 3/1992 | Miyata et al. | |
| 5,111,818 A | 5/1992 | Suzuki et al. | |
| 5,121,750 A | 6/1992 | Katims | |
| 5,127,403 A | 7/1992 | Brownlee | |
| 5,131,406 A | 7/1992 | Kaltenbach | |
| 5,143,089 A | 9/1992 | Alt | |
| 5,154,169 A | 10/1992 | Miyata et al. | |
| 5,154,387 A | 10/1992 | Trailer | |
| 5,156,157 A | 10/1992 | Valenta, Jr. et al. | |
| 5,170,802 A | 12/1992 | Mehra | |
| 5,261,419 A | 11/1993 | Osypka | |
| 5,285,781 A | 2/1994 | Brodard | |
| 5,314,460 A | 5/1994 | Borghi | |
| 5,336,251 A | 8/1994 | Borghi | |
| 5,356,427 A | 10/1994 | Miyata et al. | |
| 5,374,287 A | 12/1994 | Rubin | |
| 5,387,232 A | 2/1995 | Trailer | |
| 5,411,527 A | 5/1995 | Alt | |
| 5,423,806 A | 6/1995 | Dale et al. | |
| 5,466,255 A | 11/1995 | Franchi | |
| 5,476,502 A | 12/1995 | Rubin | |
| 5,483,022 A | 1/1996 | Mar | |
| 5,484,419 A | 1/1996 | Fleck | |
| 5,496,354 A | 3/1996 | DeBellis | |
| 5,507,787 A | 4/1996 | Borghi | |
| 5,531,779 A | 7/1996 | Dahl et al. | |
| 5,545,191 A | 8/1996 | Mann et al. | |
| 5,549,109 A | 8/1996 | Samson et al. | |
| 5,571,159 A | 11/1996 | Alt | |
| 5,588,432 A | 12/1996 | Crowley | |
| 5,634,899 A | 6/1997 | Shapland et al. | |
| 5,674,217 A | 10/1997 | Wahlstrom et al. | |
| 5,755,761 A | 5/1998 | Obino | |
| 5,755,764 A | 5/1998 | Schroeppel | |
| 5,760,341 A | 6/1998 | Laske et al. | |
| 5,772,693 A | 6/1998 | Brownlee | |
| 5,797,903 A | 8/1998 | Swanson et al. | |
| 5,800,496 A | 9/1998 | Swoyer et al. | |
| 5,814,076 A | 9/1998 | Brownlee | |
| 5,843,132 A | 12/1998 | Ilvento | |
| 5,851,206 A | 12/1998 | Guglielmi et al. | |
| 5,906,207 A | 5/1999 | Shen | |
| 5,921,935 A | 7/1999 | Hickey | |
| 5,935,160 A | 8/1999 | Auricchio et al. | |
| 5,954,761 A | 9/1999 | Machek et al. | |
| 5,976,131 A | 11/1999 | Guglielmi et al. | |
| 5,997,536 A | 12/1999 | Osswald et al. | |
| 6,014,579 A | 1/2000 | Pomeranz et al. | |
| 6,023,638 A | 2/2000 | Swanson | |
| 6,056,742 A | 5/2000 | Murphy-Chutorian et al. | |
| 6,132,390 A | 10/2000 | Cookston et al. | |
| 6,136,011 A | 10/2000 | Stambaugh | |
| 6,156,061 A | 12/2000 | Wallace et al. | |
| 6,161,029 A | 12/2000 | Spreigl et al. | |
| 6,167,315 A | 12/2000 | Coe et al. | |
| 6,178,354 B1 | 1/2001 | Gibson | |
| 6,183,469 B1 | 2/2001 | Thapliyal et al. | |
| 6,238,390 B1 | 5/2001 | Tu et al. | |
| 6,241,727 B1 | 6/2001 | Tu et al. | |
| 6,272,379 B1 | 8/2001 | Fischell et al. | |
| 6,324,434 B2 | 11/2001 | Coe et al. | |
| 6,366,808 B1 | 4/2002 | Schroeppel et al. | |
| 6,379,351 B1 | 4/2002 | Thapliyal et al. | |
| 6,397,109 B1 | 5/2002 | Cammilli et al. | |
| 6,451,016 B1 | 9/2002 | Karakozian | |
| 6,477,402 B1 | 11/2002 | Lynch et al. | |
| 6,477,427 B1 | 11/2002 | Stolz et al. | |
| 6,501,983 B1 | 12/2002 | Natarajan et al. | |
| 6,512,957 B1 | 1/2003 | Witte | |
| 6,540,765 B1 | 4/2003 | Malacoff | |
| 6,569,145 B1 | 5/2003 | Shmulewitz et al. | |
| 6,584,362 B1 | 6/2003 | Scheiner et al. | |
| 6,638,278 B2 | 10/2003 | Falwell et al. | |
| 6,640,120 B1 | 10/2003 | Swanson et al. | |
| 6,669,624 B2 | 12/2003 | Frazier | |
| 6,690,970 B1 | 2/2004 | Taheri et al. | |
| 6,697,676 B2 | 2/2004 | Dahl | |
| 6,709,390 B1 | 3/2004 | Marie Pop | |
| 6,711,436 B1 | 3/2004 | Duhaylongsod | |
| 6,711,440 B2 | 3/2004 | Deal et al. | |
| 6,772,014 B2 | 8/2004 | Coe et al. | |
| 6,865,420 B1 | 3/2005 | Kroll | |
| 6,909,920 B2 | 6/2005 | Lokhoff et al. | |
| 6,950,701 B2 | 9/2005 | Begemann et al. | |
| 6,980,858 B2 | 12/2005 | Fuimaono et al. | |
| 6,988,001 B2 | 1/2006 | Greatbatch et al. | |
| 6,994,314 B2 | 2/2006 | Garnier et al. | |
| 6,999,809 B2 | 2/2006 | Currier et al. | |
| 6,999,821 B2 | 2/2006 | Jenney et al. | |
| 7,029,467 B2 | 4/2006 | Currier et al. | |
| 7,295,874 B2 | 11/2007 | Prinzen et al. | |
| 7,422,585 B1 | 9/2008 | Eggers et al. | |
| 7,499,756 B2 | 3/2009 | Bowe et al. | |
| 7,962,208 B2 | 6/2011 | Shuros et al. | |
| 8,244,352 B2 | 8/2012 | Eidenschink et al. | |
| 2002/0026228 A1 | 2/2002 | Schauerte | |
| 2002/0042632 A1 | 4/2002 | Iaizzo et al. | |
| 2002/0072777 A1 | 6/2002 | Lu | |
| 2002/0095067 A1 | 7/2002 | Guenst et al. | |
| 2002/0116028 A1 | 8/2002 | Greatbatch et al. | |
| 2002/0116029 A1 | 8/2002 | Miller et al. | |
| 2002/0116033 A1 | 8/2002 | Greatbatch et al. | |
| 2002/0116034 A1 | 8/2002 | Miller et al. | |
| 2002/0165576 A1 | 11/2002 | Boyle et al. | |
| 2003/0004549 A1 | 1/2003 | Hill et al. | |
| 2003/0009189 A1 | 1/2003 | Gilson et al. | |
| 2003/0045908 A1 | 3/2003 | Condie et al. | |
| 2003/0060854 A1 | 3/2003 | Zhu | |
| 2003/0078471 A1 | 4/2003 | Foley et al. | |
| 2003/0109901 A1 | 6/2003 | Greatbatch | |
| 2003/0139778 A1 | 7/2003 | Fischell et al. | |
| 2003/0158584 A1 | 8/2003 | Cates et al. | |
| 2003/0204206 A1 | 10/2003 | Padua et al. | |
| 2003/0204231 A1 | 10/2003 | Hine et al. | |
| 2003/0212361 A1 | 11/2003 | Boyle et al. | |
| 2003/0229386 A1 | 12/2003 | Rosenman et al. | |
| 2003/0233130 A1 | 12/2003 | Padmanabhan et al. | |
| 2004/0010189 A1 | 1/2004 | van Sloun et al. | |
| 2004/0015081 A1 | 1/2004 | Kramer et al. | |
| 2004/0015204 A1 | 1/2004 | Whitehurst et al. | |
| 2004/0038947 A1 | 2/2004 | Wink et al. | |
| 2004/0088017 A1 | 5/2004 | Sharma et al. | |
| 2004/0097805 A1 | 5/2004 | Verard et al. | |
| 2004/0106960 A1 | 6/2004 | Siejko et al. | |
| 2004/0116994 A1 | 6/2004 | De Bellis | |
| 2004/0133247 A1 | 7/2004 | Stahmann et al. | |
| 2004/0162599 A1 | 8/2004 | Kurth | |
| 2004/0172081 A1 | 9/2004 | Wang | |
| 2004/0214148 A1 | 10/2004 | Salvino et al. | |
| 2004/0215139 A1 | 10/2004 | Cohen | |
| 2004/0255956 A1 | 12/2004 | Vinten-Johansen et al. | |
| 2004/0267326 A1 | 12/2004 | Ocel et al. | |
| 2005/0004476 A1 | 1/2005 | Payvar et al. | |
| 2005/0038345 A1 | 2/2005 | Gorgenberg et al. | |
| 2005/0075673 A1 | 4/2005 | Warkentin et al. | |
| 2005/0119545 A1 | 6/2005 | Swanson | |
| 2005/0137631 A1 | 6/2005 | Yu et al. | |
| 2005/0137647 A1 | 6/2005 | Wallace et al. | |
| 2005/0149155 A1 | 7/2005 | Scheiner et al. | |
| 2005/0197674 A1 | 9/2005 | McCabe et al. | |
| 2005/0222632 A1 | 10/2005 | Obino | |
| 2005/0251239 A1 | 11/2005 | Wallace et al. | |
| 2005/0288717 A1 | 12/2005 | Sunagawa | |
| 2005/0288763 A1 | 12/2005 | Andreas et al. | |
| 2006/0009830 A1 | 1/2006 | Atkinson et al. | |

| | | | |
|---|---|---|---|
| 2006/0036306 A1 | 2/2006 | Heist et al. | |
| 2006/0058597 A1 | 3/2006 | Machado et al. | |
| 2006/0100639 A1 | 5/2006 | Levin et al. | |
| 2006/0100669 A1 | 5/2006 | Fuimaono et al. | |
| 2006/0116593 A1 | 6/2006 | Zhang et al. | |
| 2006/0136049 A1 | 6/2006 | Rojo | |
| 2006/0142660 A1 | 6/2006 | Maschke | |
| 2006/0142812 A1 | 6/2006 | Ortega et al. | |
| 2006/0149326 A1 | 7/2006 | Prinzen et al. | |
| 2006/0178586 A1 | 8/2006 | Dobak | |
| 2006/0184191 A1 | 8/2006 | O'Brien | |
| 2006/0195038 A1 | 8/2006 | Carlson et al. | |
| 2006/0241704 A1* | 10/2006 | Shuros et al. | 607/9 |
| 2006/0241733 A1 | 10/2006 | Zhang et al. | |
| 2006/0241736 A1 | 10/2006 | Haldeman | |
| 2006/0247700 A1 | 11/2006 | Jackson | |
| 2006/0253156 A1 | 11/2006 | Pastore et al. | |
| 2006/0259085 A1 | 11/2006 | Zhang et al. | |
| 2006/0259087 A1 | 11/2006 | Baynham et al. | |
| 2006/0259088 A1 | 11/2006 | Pastore et al. | |
| 2006/0287684 A1 | 12/2006 | Baynham et al. | |
| 2006/0293741 A1 | 12/2006 | Johnson et al. | |
| 2007/0021789 A1 | 1/2007 | Pastore et al. | |
| 2007/0021811 A1 | 1/2007 | D'Aquanni et al. | |
| 2007/0054871 A1 | 3/2007 | Pastore et al. | |
| 2007/0055334 A1 | 3/2007 | Haldeman et al. | |
| 2007/0100410 A1 | 5/2007 | Lamson et al. | |
| 2007/0150005 A1 | 6/2007 | Sih et al. | |
| 2007/0150009 A1 | 6/2007 | Kveen et al. | |
| 2007/0233200 A1 | 10/2007 | Maschke | |
| 2007/0239210 A1 | 10/2007 | Libbus et al. | |
| 2007/0260285 A1 | 11/2007 | Libbus et al. | |
| 2008/0058757 A1 | 3/2008 | Pajunk et al. | |
| 2008/0071315 A1 | 3/2008 | Baynham et al. | |
| 2008/0082136 A1 | 4/2008 | Gaudiani | |
| 2008/0109063 A1 | 5/2008 | Hancock et al. | |
| 2008/0114408 A1 | 5/2008 | Shuros et al. | |
| 2008/0288030 A1 | 11/2008 | Zhang et al. | |
| 2008/0319502 A1 | 12/2008 | Sunagawa et al. | |
| 2009/0005845 A1 | 1/2009 | David et al. | |
| 2009/0143835 A1 | 6/2009 | Pastore et al. | |
| 2009/0299443 A1 | 12/2009 | Mokelke et al. | |
| 2009/0318749 A1 | 12/2009 | Stolen et al. | |
| 2009/0318943 A1 | 12/2009 | Eidenschink et al. | |
| 2009/0318984 A1 | 12/2009 | Mokelke et al. | |
| 2009/0318989 A1 | 12/2009 | Tomaschko et al. | |
| 2009/0318990 A1 | 12/2009 | Tomaschko et al. | |
| 2009/0318992 A1 | 12/2009 | Eidenschink et al. | |
| 2009/0318993 A1 | 12/2009 | Eidenschink et al. | |
| 2009/0318994 A1 | 12/2009 | Eidenschink et al. | |
| 2010/0056858 A1 | 3/2010 | Mokelke et al. | |
| 2011/0230928 A1 | 9/2011 | Shuros et al. | |

FOREIGN PATENT DOCUMENTS

| | | |
|---|---|---|
| JP | 2001517995 A | 10/2001 |
| JP | 2002263201 A | 9/2002 |
| JP | 20086275 A | 1/2006 |
| JP | 2006526483 A | 11/2006 |
| JP | 2009521276 A | 6/2009 |
| JP | 2011524787 A | 9/2011 |
| WO | WO-95/18649 A1 | 7/1995 |
| WO | WO-01/15609 A1 | 3/2001 |
| WO | WO-03/035139 A1 | 5/2003 |
| WO | WO-2004/058326 A2 | 7/2004 |
| WO | WO-2005000398 A2 | 1/2005 |
| WO | WO-2005/065771 A1 | 7/2005 |
| WO | WO-2006/115693 A2 | 11/2006 |
| WO | WO-2006/124636 A2 | 11/2006 |
| WO | WO-2006/124729 A2 | 11/2006 |
| WO | WO-2007/133962 A2 | 11/2007 |
| WO | WO-2008/027261 A1 | 3/2008 |
| WO | WO-2009/114081 A1 | 9/2009 |
| WO | WO-2009/154718 A1 | 12/2009 |
| WO | WO-2009/154720 A1 | 12/2009 |
| WO | WO-2009/154722 A1 | 12/2009 |
| WO | WO-2009/154725 A2 | 12/2009 |
| WO | WO-2009/154729 A1 | 12/2009 |
| WO | WO-2009/154730 A1 | 12/2009 |
| WO | WO-2009/154732 A1 | 12/2009 |
| WO | WO-2009154725 A3 | 2/2010 |

OTHER PUBLICATIONS

"U.S. Appl. No. 11/113,828, Notice of Allowance mailed Feb. 4, 2011", 7 pgs.

"U.S. Appl. No. 11/113,828, Notice of Allowance mailed Oct. 19, 2010", 4 pgs.

"U.S. Appl. No. 12/484,727, Restriction Requirement mailed Dec. 23, 2011", 7 pgs.

"U.S. Appl. No. 12/484,760, Non Final Office Action mailed Dec. 7, 2011", 7 pgs.

"U.S. Appl. No. 12/484,769, Non Final Office Action mailed Nov. 10, 2011", 7 pgs.

"U.S. Appl. No. 12/484,778, Restriction Requirement mailed Jan. 19, 2012", 5 pgs.

"U.S. Appl. No. 12/484,786, Non Final Office Action Mailed Jan. 4, 2012", 7 pgs.

"U.S. Appl. No. 12/484,804, Response to Restriction Requirement filed Dec. 14, 2011", 7 pgs.

"U.S. Appl. No. 12/484,804, Restriction Requirement mailed Nov. 14, 2011", 8 pgs.

"U.S. Appl. No. 12/484,811, Non Final Office Action mailed Dec. 12, 2011", 8 pgs.

"U.S. Appl. No. 12/547,316 , Response filed Aug. 29, 2011 to Restriction Requirement mailed Jul. 28, 2011", 12 pgs.

"U.S. Appl. No. 12/547,316, Non Final Office Action mailed Sep. 28, 2011", 11 pgs.

"U.S. Appl. No. 12/547,316, Restriction Requirement mailed Jul. 28, 2011", 7 pgs.

"U.S. Appl. No. 12/547,316,Response to Non Final Office Action mailed Sep. 28, 2011", 11 pgs.

"U.S. Appl. No. 13/113,706, Non Final Office Action Mailed Dec. 21, 2011", 6 pgs.

"European Application Serial No. 09767033.5, Office Action Response filed Dec. 5, 2011", 10 pgs.

"European Application Serial No. 09767038.4, Office Action response filed Jan. 18, 2012", 7 pgs.

"European Application Serial No. 09767033.5, Examination Notification Art. 94(3) mailed Aug. 2, 2011", 6 pgs.

"U.S. Appl. No. 11/113,828, Advisory Action mailed Feb. 2, 2010", 3 pgs.

"U.S. Appl. No. 11/113,828, Final Office Action mailed Jun. 29, 2009", 11 pgs.

"U.S. Appl. No. 11/113,828, Final Office Action mailed Sep. 17, 2008", 10 pgs.

"U.S. Appl. No. 11/113,828, Final Office Action mailed Nov. 24, 2009", 13 pgs.

"U.S. Appl. No. 11/113,828, Non-Final Office Action mailed Mar. 5, 2008", 8 pgs.

"U.S. Appl. No. 11/113,828, Non-Final Office Action mailed Dec. 22, 2008", 10 pgs.

"U.S. Appl. No. 11/113,828, Response filed Jan. 25, 2010 to Final Office Action mailed Nov. 24, 2009", 8 pgs.

"U.S. Appl. No. 11/113,828, Response filed Jan. 28, 2008 to Restriction Requirement mailed Dec. 26, 2007", 7 pgs.

"U.S. Appl. No. 11/113,828, Response filed Mar. 23, 2009 to Non-Final Office Action mailed Dec. 22, 2008", 8 pgs.

"U.S. Appl. No. 11/113,828, Response filed Jun. 5, 2008 to Non-Final Office Action mailed Mar. 5, 2008", 8 pgs.

"U.S. Appl. No. 11/113,828, Response filed Oct. 29, 2009 to Final Office Action mailed Jun. 29, 2009", 9 pgs.

"U.S. Appl. No. 11/113,828, Response filed Nov. 17, 2008 to Final Office Action mailed Sep. 17, 2008", 11 pgs.

"U.S. Appl. No. 11/113,828, Restriction Requirement mailed Dec. 26, 2007", 8 pgs.

"International Application Serial No. PCT/US/2009/003589, International Search Report mailed Sep. 14, 2009", 5 pgs.

"International Application Serial No. PCT/US/2009/003589, Written Opinion mailed Sep. 14, 2009", 11 pgs.

"International Application Serial No. PCT/US2009/001321, International Search Report mailed Jul. 2, 2009", 4 pgs.

"International Application Serial No. PCT/US2009/001321, Written Opinion mailed Jul. 2, 2009", 7 pgs.

"International Application Serial No. PCT/US2009/003575, International Search Report mailed Sep. 14, 2009", 6 pgs.
"International Application Serial No. PCT/US2009/003575, Written Opinion mailed Sep. 14, 2009", 9 pgs.
"International Application Serial No. PCT/US2009/003577, International Search Report mailed Aug. 9, 2009", 5 pgs.
"International Application Serial No. PCT/US2009/003577, Written Opinion mailed Aug. 9, 2009", 10 pgs.
"International Application Serial No. PCT/US2009/003581, International Search Report mailed Sep. 21, 2009", 5 pgs.
"International Application Serial No. PCT/US2009/003581, Written Opinion mailed Sep. 21, 2009", 10 pgs.
"International Application Serial No. PCT/US2009/003585, International Search Report mailed Dec. 21, 2009", 4 pgs.
"International Application Serial No. PCT/US2009/003585, Written Opinion mailed Dec. 21, 2009", 7 pgs.
"International Application Serial No. PCT/US2009/003590, International Search Report mailed Sep. 14, 2009", 5 pgs.
"International Application Serial No. PCT/US2009/003590, Written Opinion mailed Sep. 14, 2009", 10 pgs.
Baynham, T. C., et al., "Integrated Catheter and Pulse Generator Systems and Methods", U.S. Appl. No. 11/468,875, filed Aug. 31, 2006, 23 pgs.
Baynham, T. C., et al., "Method and Apparatus for Initiating and Delivering Cardiac Protection Pacing", U.S. Appl. No. 11/382,849, filed May 11, 2006, 37 pgs.
Brockway, M. V., et al., "Method and Apparatus for Delivering Chronic and Post-Ischemia Cardiac Therapies", U.S. Appl. No. 11/207,251, filed Aug. 19, 2005, 40 pgs.
Heinroth, K. M, et al., "Temporary transcoronary pacing by coated guidewires", *Clin Res Cardiol.*, 95, (2006), 1-6.
Henriques, J. P., et al., "Outcome of primary angioplasty for acute myocardial infarction during routine duty hours versus during off-hours", *J Am Coll Cardiol*, 41(12), (Jun. 18, 2003), 2138-2142.
Kin, H., et al., "Postconditioning attenuates myocardial ischemia-reperfusion injury by inhibiting events in the early minutes of reperfusion", *Cardiovascular research*, 62(1), (Apr. 1, 2004), 74-85.
Kis, A., "Repeated cardiac pacing extends the time during which canine hearts are protected against ischaemia-induced arrhythmias : role of nitric oxide.", *Journal of Molecular and Cellular Cardiology*, 31(6), (1999), 1229-1241.
Koning, M. M., "Rapid ventricular pacing produces myocardial protection by nonischemic activation of $K_{ATP}^+$ channels", *Circulation.* 93(1), (Jan. 1, 1996), 178-186.
Meier, B., et al., "Coronary pacing during percutaneous transluminal coronary angioplasty", *Circulation*, 71(3), (1985), 557-561.
Murry, C. E., et al., "Preconditioning with ischemia: a delay of lethal cell injury in ischemic myocardium", *Circulation*, 74(5), (1986), 1124-1136.
Ovize, M., et al., "Stretch preconditions canine myocardium.", *Am J Physiol.*, 266(1 Pt 2), (Jan. 1994), H137-H146.
Pastore, J. M, et al., "Intermittent Stress Augmentation Pacing for Cardioprotective Effect", U.S. Appl. No. 11/458,288, filed Jul. 18, 2006, 23 pgs.
Rosa, A., et al., "Ectopic Pacing at Physiological Rate Improves Postanoxic Recovery of the Developing Heart", *Am. J. Physiol.—Heart Circ. Physiol.*, 284, (2003), H2384-H2392.
Tsang, A., et al., "Postconditioning: a form of "modified reperfusion" protects the myocardium by activating the phosphatidylinositol 3-kinase-Akt pathway", *Circ Res.*, 95(3), Epub Jul. 8, 2004., (Aug. 6, 2004), 230-2.
Vanagt, W. Y. R., et al., "Ventricular Pacing for Improving Myocardial Tolerance to Ischemia", *Progress Report on Project Guidant-CARIM*, (Oct. 2003), 1-25.
Vegh, A., et al., "Transient ischaemia induced by rapid cardiac pacing results in myocardial preconditioning", *Cardiovascular Research*, 25(12), (Dec. 1991), 1051-1053.
Wu, Zhong-Kai, et al., "Ischemic preconditioning suppresses ventricular tachyarrhythmias after myocardial revascularization", *Circulation*, 106(24), (Dec. 10, 2002), 3091-3096.
Yang, S. M., et al., "Multiple, brief coronary occlusions during early reperfusion protect rabbit hearts by targeting cell signaling pathways", *Journal of the American College of Cardiology*, 44(5), (Sep. 1, 2004), 1103-1110.
Zhao, Zhi-Qing, et al., "Inhibition of myocardial injury by ischemic postconditioning during reperfusion: comparison with ischemic preconditioning", *Am J. Physiol Heart Circ Physiol*, 285(2), (Aug. 2003), H579-H588.
"U.S. Appl. No. 12/484,727, Non Final Office Action mailed Feb. 13, 2012", 8 pgs.
"U.S. Appl. No. 12/484,727, Response to Restriction Requirement filed Jan. 23, 2012", 6 pgs.
"U.S. Appl. No. 12/484,760, Notice of Allowance mailed Apr. 11, 2012", 5 pgs.
"U.S. Appl. No. 12/484,769, Final Office Action mailed Apr. 26, 2012", 8 pgs.
"U.S. Appl. No. 12/484,879, Response filed Feb. 10, 2012 to Non Final Office Action mailed Nov. 10, 2011", 11 pgs.
"U.S. Appl. No. 12/484,778, Non Final Office Action Mailed Mar. 13, 2012", 7 pgs.
"U.S. Appl. No. 12/484,786, Response filed Apr. 18, 2012 to Non Final Office Action mailed Jan. 4, 2012", 9 pgs.
"U.S. Appl. No. 12/484,804. Non Final Office Action Mailed Feb. 6, 2012", 9 pgs.
"U.S. Appl. No. 13/113,706 , Response filed Mar. 21, 2012 to Non Final Office Action mailed Dec. 21, 2011", 14 pgs.
"U.S. Appl. No. 12/484,760 , Response filed Mar. 5, 2012 to Non Final Office Action mailed Dec. 7, 2011", 12 pgs.
"U.S. Appl. No. 12/484,727, Final Office Action mailed Aug. 16, 2012", 9 pgs.
"U.S. Appl. No. 12/484,727, Response filed Jun. 12, 2012 to Non Final Office Action mailed Feb. 13, 2012", 10 pgs.
"U.S. Appl. No. 12/484,769 , Response filed Jun. 21, 2012 to Final Office Action mailed Apr. 26, 2012", 10 pgs.
"U.S. Appl. No. 12/484,769, Advisory Action mailed Jun. 29, 2012", 2 pgs.
"U.S. Appl. No. 12/484,778, Final Office Action mailed Aug. 15, 2012", 7 pgs.
"U.S. Appl. No. 12/484,778, Response filed Jun. 12, 2012 to Non Final Office Action Mailed Mar. 13, 2012", 9 pgs.
"U.S. Appl. No. 12/484,786 , Response filed Aug. 15, 2012 to Final Office Action mailed Jun. 18, 2012", 10 pgs.
"U.S. Appl. No. 12/484,786, Advisory Action mailed Aug. 22, 2012", 3 pgs.
"U.S. Appl. No. 12/484,786, Final Office Action mailed Jun. 18, 2012", 8 pgs.
"U.S. Appl. No. 12/484,786, Response filed Sep. 18, 2012 to Final Office Action mailed Jun. 18, 2012", 10 pgs.
"U.S. Appl. No. 12/484,804, Final office Action mailed Jun. 5, 2012", 10 pgs.
"U.S. Appl. No. 12/484,804, Response filed May 3, 2012 to Non-Final Office Action mailed Feb. 6, 2012", 12 pgs.
"U.S. Appl. No. 12/484,804, Response filed Oct. 2, 2012 to Final Office Action mailed Jun. 5, 2012", 12 pgs.
"European Application Serial No. 09767033.5, Office Action mailed Apr. 15, 2011", 1 pg.
"European Application Serial No. 09767033.5, Response filed May 18, 2011 to Office Action mailed Apr. 15, 2011", 7 pgs.
"European Application Serial No. 09767043.4, Office Action mailed Apr. 14, 2011", 1 pg.
"European Application Serial No. 09767043.4, Response filed May 24, 2011 to Office Action mailed Apr. 14, 2011", 13 pgs.
"International Application Serial No. PCT/US2009/003577, International Preliminary Report on Patentability mailed Jan. 6, 2011", 12 pgs.
"International Application Serial No. PCT/US2009/003590, International Preliminary Report on Patentability mailed Jan. 6, 2011", 9 pgs.
"Japanese Application Serial No. 2011-514590, Office Action mailed Sep. 19, 2012", With English Translation, 5 pgs.
"Japanese Application Serial No. 2011-514591, Voluntary Amendment filed Jan. 12, 2011", (w/ English Translation), 11 pgs.
"Japanese Application Serial No. 2011-514593, Office Action mailed Sep. 19, 2012", With English Translation, 7 pgs.
"Japanese Application Serial No. 2011-514594, Voluntary Amendment filed Jan. 18, 2011", (w/ English Translation of Amended Claims), 49 pgs.
U.S. Appl. No. 13/113,706, filed May 23, 2011, Method and Apparatus for Pacing During Revascularization.

* cited by examiner

PACING CATHETER FOR ACCESS TO MULTIPLE VESSELS

CROSS-REFERENCE TO RELATED APPLICATIONS

This application claims the benefit of U.S. Provisional Application No. 61/074,035, filed on Jun. 19, 2008, under 35 U.S.C. §119(e), which is hereby incorporated by reference.

This application is related to co-pending, commonly assigned, U.S. patent application Ser. No. 11/113,828, entitled "METHOD AND APPARATUS FOR PACING DURING REVASCULARIZATION", filed on Apr. 25, 2005, U.S. patent application Ser. No. 11/468,875, entitled "INTEGRATED CATHETER AND PULSE GENERATOR SYSTEMS AND METHODS", filed on Aug. 31, 2006, U.S. Patent Application Ser. No. 61/074,032, entitled "PACING CATHETER WITH EXPANDABLE DISTAL END", filed on Jun. 19, 2008, U.S. Patent Application Ser. No. 61/074,042, entitled "PACING CATHETER RELEASING CONDUCTIVE LIQUID", filed on Jun. 19, 2008, U.S. Patent Application Ser. No. 61/074,048, entitled "PACEMAKER INTEGRATED WITH VASCULAR INTERVENTION CATHETER", filed on Jun. 19, 2008, U.S. Patent Application Ser. No. 61/074,055, entitled "TRANSVASCULAR BALLOON CATHETER WITH PACING ELECTRODES ON SHAFT", filed on Jun. 19, 2008, U.S. Patent Application Ser. No. 61/074,060, entitled "PACING CATHETER WITH STENT ELECTRODE", filed on Jun. 19, 2008, U.S. Patent Application Ser. No. 61/074,064, entitled "VASCULAR INTERVENTION CATHETERS WITH PACING ELECTRODES", filed on June 19, U.S. Patent Application Ser. No. 61/074,066, entitled "EXTERNAL PACEMAKER WITH AUTOMATIC CARDIOPROTECTIVE PACING PROTOCOL", filed on even date herewith, U.S. Patent Application Ser. No. 61/074,024, entitled "METHOD AND DEVICE FOR PACING AND INTERMITTENT ISCHEMIA", filed on Jun. 19, 2008, which are hereby incorporated by reference in their entirety.

TECHNICAL FIELD

This document relates generally to cardiac pacing systems and particularly to a system for delivering cardioprotective pacing during revascularization procedure.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are resulted from contractions of the myocardium (cardiac muscles). In a normal heart, the sinoatrial node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions. A blocked or otherwise abnormal electrical conduction and/or deteriorated myocardial tissue cause dyssynchronous contraction of the heart, resulting in poor hemodynamic performance, including a diminished blood supply to the heart and the rest of the body. The condition in which the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen supply and metabolite removal due to an interruption in blood supply caused by an occlusion of a blood vessel such as a coronary artery. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure.

When a blood vessel such as the coronary artery is partially or completely occluded, a revascularization procedure such as percutaneous transluminal coronary angioplasty (PTCA) can be performed to reopen the occluded blood vessel. However, the revascularization procedure itself involves a temporary occlusion of the coronary artery. Reperfusion that follows the reopening of the occluded blood vessel is also known to cause cardiac injury, known as reperfusion injury. In addition, plaques dislodged and displaced by the revascularization procedure may enter small blood vessels branching from the blood vessel in which the revascularization is performed, causing occlusion of these small blood vessels. The revascularization procedure may also cause distal embolization, i.e., obstruction of the artery caused by the plaque dislodged during the procedure. Therefore, there is a need for minimizing cardiac injury associated with MI and the subsequent revascularization procedure.

SUMMARY

Cardioprotective pacing is applied to prevent and/or reduce cardiac injury associated with myocardial infarction (MI) and revascularization procedure. Pacing pulses are generated from a pacemaker and delivered through one or more pacing electrodes incorporated onto one or more percutaneous transluminal vascular intervention (PTVI) devices during the revascularization procedure. The pacemaker controls the delivery of the pacing pulses by automatically executing a cardioprotective pacing protocol.

In one embodiment, cardioprotective pacing is delivered during revascularization of a blood vessel. A PTVI device assembly includes a plurality of pacing leads and a catheter. The pacing leads each include a distal end portion and one or more pacing electrodes incorporated onto the distal end portion. The catheter includes one or more entry ports and a plurality of exit ports and allows the distal end portion of each pacing lead of the plurality of pacing leads to enter an entry port of the one or more entry ports and exit from an exit port of the plurality of exit ports.

In one embodiment, a system delivers cardioprotective pacing to two blood vessels during a revascularization procedure. The system includes two pacing leads and a catheter. The two pacing leads each include a distal end portion with a pacing electrode. The catheter accommodates a portion of each of the two pacing leads and allows the distal end portion of each of the two pacing leads to exit from the catheter and enter a blood vessel.

In one embodiment, a method for delivering cardioprotective pacing during revascularization is provided. A PTVI device assembly is provided. The PTVI device assembly includes a catheter and a plurality of pacing leads. The catheter includes one or more entry ports and a plurality of exit ports. The pacing leads each include a distal end portion introduced into one of the blood vessels by entering an entry port of the one or more entry ports and exiting from an exit port of the plurality of exit ports. The distal end portion of each pacing lead includes one or more pacing electrodes. Pacing pulses are delivered through the plurality of pacing leads.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
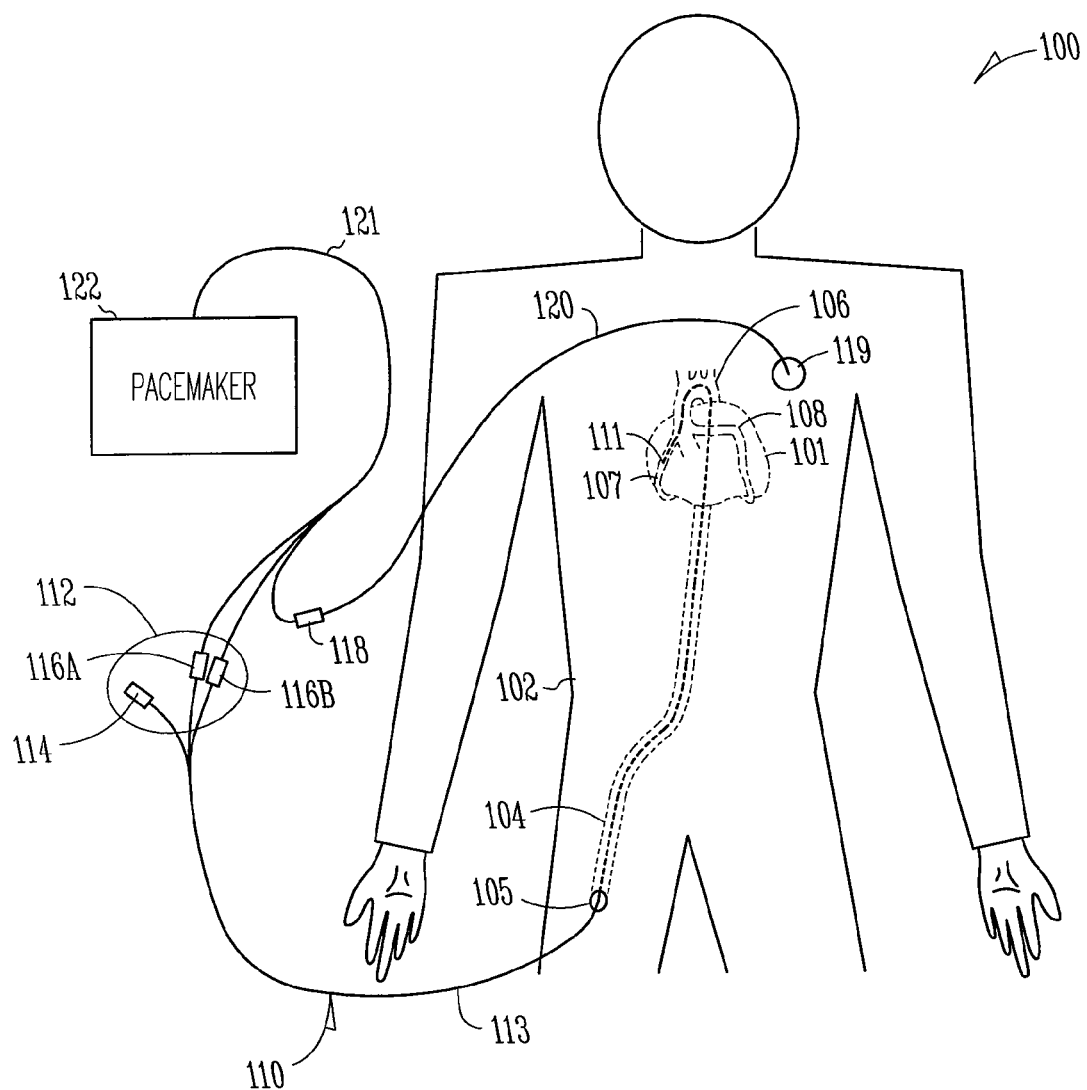
FIG. 1 is an illustration of an embodiment of a system providing for pacing during revascularization and portions of an environment in which the system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

In this document, "revascularization" includes reopening of a completely or partially occluded blood vessel using percutaneous transluminal vascular intervention (PTVI) procedure, such as a percutaneous transluminal coronary angioplasty (PTCA) procedure performed in response to cardiac ischemia or myocardial infarction (MI), using PTVI devices such as those discussed in this document.

This document discusses a pacing system that delivers pacing pulses through one or more PTVI devices to a patient receiving a revascularization procedure. In an application, the pacing system provides for acute pacing cardioprotection therapy, also referred to as pacing postconditioning, during the revascularization procedure. The acute pacing cardioprotection therapy includes the delivery of pacing pulses before, during, and/or after the temporary occlusion of a coronary artery to prevent and/or reduce cardiac injury associated with MI and the subsequent revascularization procedure. The pacing system is capable of delivering the acute pacing cardioprotection therapy without substantially interfering with the revascularization procedure. In another application, the pacing system also provides for ischemic cardioprotection therapy. The ischemic cardioprotection therapy includes intermittent occlusion of the coronary artery, for example, by periodically inflating and deflating a balloon of a PTVI device.

To deliver pacing pulses during the revascularization procedure, one or more pacing electrodes are incorporated onto the one or more PTVI devices. Examples of such PTVI devices include guide wires, guide catheters, and angioplasty catheters such as dilatation balloon catheters, stent delivery systems, brachytherapy devices, atherectomy devices, and distal embolization protection devices. A pacemaker connected to the one or more PTVI devices generates the pacing pulses. In one embodiment, the pacemaker controls the delivery of the acute pacing cardioprotection therapy by automatically executing a cardioprotective pacing protocol specifying a pacing sequence including alternating pacing and non-pacing periods, or alternating pacing modes. In one embodiment, the pacemaker is an external pacing device such as a pacing system analyzer (PSA). In another embodiment, the pacemaker is integrated into the one of the one or more PTVI devices.

FIG. 1 is an illustration of an embodiment of a system 100 providing for pacing during revascularization and portions of an environment in which system 100 is used. System 100 includes a PTVI device 110, a pacemaker 122, and a cable 121 connecting PTVI device 110 and pacemaker 122. When needed, system 100 also includes a reference electrode 119, which is a surface electrode, such as a skin patch electrode, connected to a lead 120. Lead 120 is connected to a connector 118 allowing its connection to cable 121.

PTVI device 110 is used during a revascularization procedure and includes a distal end portion 111 for intravascular placement and a proximal end portion 112. Proximal end portion 112 includes a proximal end device 114 and pacing connectors 116A-B. Proximal end device 114 includes various connectors and other structures allowing manipulation of PTVI device 110 including the percutaneous transluminal insertion of the device and operation of an angioplasty device at distal end 111. Pacing connectors 116A-B provide for electrical connections between pacemaker 122 and PTVI device 110 through cable 121. In the illustrated embodiment, PTVI device 110 is a PTCA device used in a PTCA procedure. During the PTCA procedure, an opening 105 is made on a femoral artery 104 in a patient's body 102. PTVI device 110 is inserted into femoral artery 104 and advanced to an aorta 106 and then to a right coronary artery 107, which is narrowed or blocked. The angioplasty device at distal end 111 is then used to open up the blocked right coronary artery 107. In another embodiment, PTVI device 110 is used to open up a blocked left coronary artery 108.

Distal end portion 111 of PTVI device 110 includes one or more pacing electrodes to allow pacing pulses to be delivered to a heart 101 during the PTCA procedure. In one embodiment, pacing pulses are delivered through two pacing electrodes on distal end portion 111 of PTVI device 110. In another embodiment, pacing pulses are delivered through a pacing electrode on distal end portion 111 of PTVI device 110 and surface electrode 119 functioning as the return electrode for pacing.

Pacemaker 122 delivers pacing pulses by executing a cardioprotective pacing protocol. In one embodiment, the cardioprotective pacing protocol specifies a cardioprotective pacing sequence for preventing arrhythmias and cardiac injuries associated with the revascularization procedure. In one embodiment, pacemaker 122 is an external pacemaker such as a PSA. In another embodiment, pacemaker 122 includes an implantable pacemaker adapted for external use.

It is to be understood that FIG. 1 is for illustrative, but not restrictive, purposes. For example, the physical structure of proximal end portion 112 depends on functional and ease-of-use considerations. Proximal end device 114 represents a structure that accommodates all the mechanical connection and access requirements, which depend on the specific configuration and function of PTVI device 110. In one embodiment, proximal end device 114 includes an integrated device as illustrated in FIG. 1. In another embodiment, proximal end device 114 branches out into multiple connectors and/or other devices. Pacing connectors 116A-B represent a structure that accommodates all the electrical connections required for delivering pacing pulses from pacemaker 122 to PTVI device 110. The number of pacing connectors depends on the number of pacing electrodes incorporated onto PTVI device 110 and how it is to be connected to cable 121. In one embodiment, when more than one electrical connection is needed for delivering the pacing pulses, proximal end portion 112 includes branched-out pacing connectors such as pacing connectors 116 and 117 as illustrated in FIG. 1. In another embodiment, proximal end portion 112 includes a single connector providing for multiple, independent electrical connections.

Pacemaker

Figure 2:
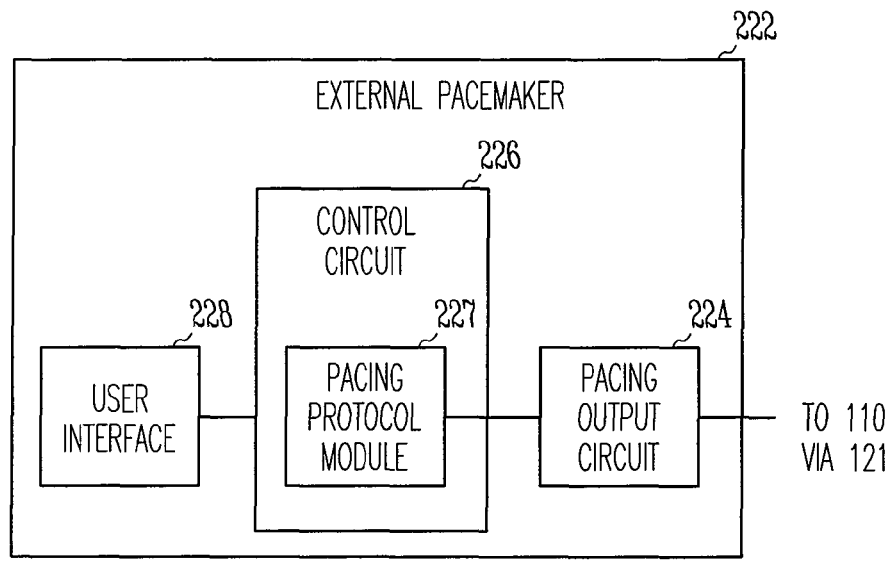
FIG. 2 is a block diagram illustrating an embodiment of a pacemaker providing for pacing during revascularization.

FIG. 2 is a block diagram illustrating an embodiment of an external pacemaker 222 that provides for pacing during revascularization. External pacemaker 222 is an embodiment of pacemaker 122 and includes a pacing output circuit 224, a user interface 228, and a control circuit 226. Pacing output circuit 224 delivers pacing pulses to PTVI device 110 through cable 121. User interface 228 allows a user to control the delivery of the pacing pulses by controlling pacing parameters and/or timing of the delivery. Control circuit 226 controls the delivery of the pacing pulses. In one embodiment, external pacemaker 222 is a PSA including a chassis that houses pacing output circuit 224 and control circuit 226. User interface 228 is incorporated onto the chassis.

In the illustrated embodiment, control circuit 226 includes a pacing protocol module 227, which enables control circuit 226 to control the delivery of the pacing pulses by automatically executing a pacing protocol. To provide an acute pacing cardioprotection therapy, the pacing protocol specifies a cardioprotective pacing sequence that includes alternating pacing and non-pacing periods or alternating pacing modes for delivering pacing during a revascularization procedure such as a PTCA procedure.

In one embodiment, pacing protocol module 227 is configured to be detachably connected to external pacemaker 222. In a specific embodiment, pacing protocol module 227 includes a memory device that stores the cardioprotective pacing protocol, and control circuit 226 is capable of automatically executing the cardioprotective pacing protocol when pacing protocol module 227 is connected to external pacemaker 222. In another specific embodiment, in addition to the memory device that stores the cardioprotective pacing protocol, pacing protocol module 227 includes a user interface that allows the user to adjust parameters of the cardioprotective pacing protocol and/or control circuitry that supplement the functions of control circuit 226 for automatically executing the cardioprotective pacing protocol. In various embodiments, other pacing protocol modules are provided for automatically executing pacing protocols using external pacemaker 222. In various embodiments, the user is provided with external pacemaker 222 and pacing protocol modules for executing pacing protocols such as the cardioprotective pacing protocol, cardiac resynchronization therapy (CRT) pacing protocol, and cardiac remodeling control therapy (RCT) pacing protocol. Compared to a PSA that requires the user to manually adjust pacing parameters during a test or therapy session, the automatic execution of the pacing protocol increases the accuracy of pacing control and reduces or eliminates the need for the user to control the delivery of the pacing pulses, so that the user can be more attentive to the response of the patient and/or the revascularization procedure.

Figure 3:
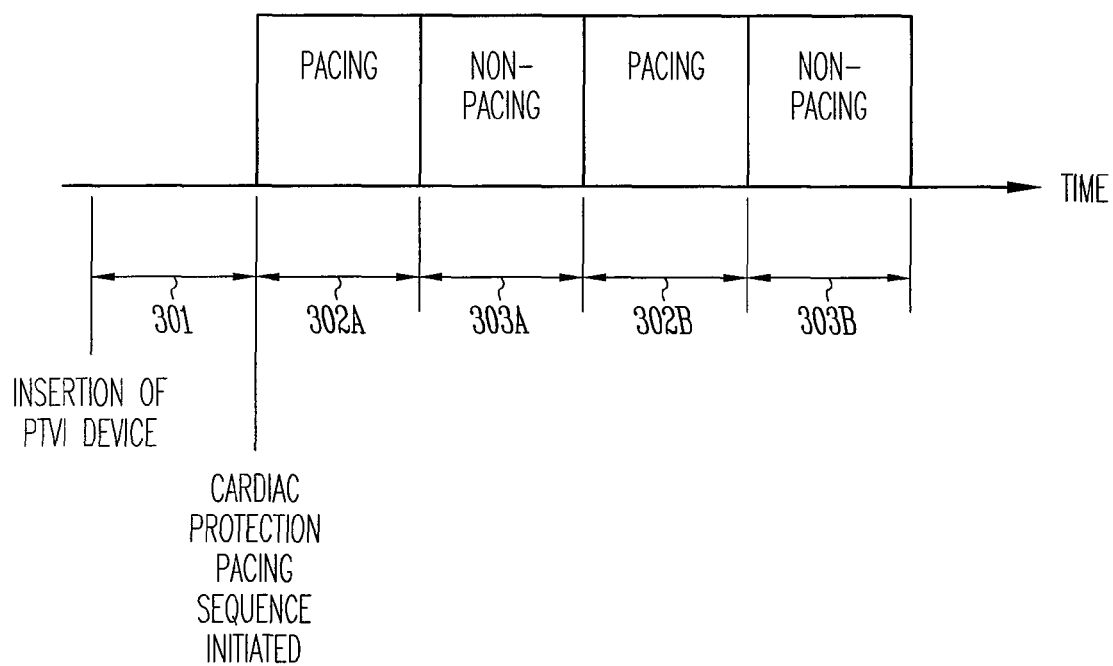
FIG. 3 is a timing diagram illustrating an embodiment of a cardioprotective pacing protocol.

FIG. 3 is a timing diagram illustrating an embodiment of the cardioprotective pacing protocol that specifies a cardioprotective pacing sequence. The cardioprotective pacing sequence is initiated after a time interval 301 that starts when the insertion of PTVI device into body 102 is completed. Time interval 301 expires before, during, and/or after an ischemic event that occurs when the blood vessel targeted by the revascularization procedure is substantially occluded by PTVI device 110. In one embodiment, the cardioprotective pacing sequence is applied repeatedly, before, during, and/or after the occlusion of the blood vessel, during the revascularization procedure.

As illustrated in FIG. 3, the cardioprotective pacing sequence includes alternating pacing and non-pacing periods. Each pacing period is a pacing duration during which the pacing pulses are delivered in a predetermined pacing mode. The non-pacing period is a non-pacing duration during which no pacing pulses is delivered. In one embodiment, during each pacing period, rapid, asynchronous pacing is applied. In other words, pacing pulses are delivered at a rate substantially higher than the patient's intrinsic heart rate without being synchronized to the patient's intrinsic cardiac contractions. For illustrative purpose only, FIG. 3 shows a cardioprotective pacing sequence that includes two cycles of alternating pacing and non-pacing periods: pacing period 302A, non-pacing periods 303A, pacing period 302B, and non-pacing periods 303B. In one embodiment, the number of the cycles of alternating pacing and non-pacing periods is programmable, and each of the pacing and non-pacing periods is programmable. In one embodiment, the cardioprotective pacing sequence is initiated before the ischemic event and includes approximately 1 to 4 cycles of alternating pacing and non-pacing periods. The pacing period is in a range of approximately 30 seconds to 20 minutes. The non-pacing period is in a range of approximately 30 seconds to 20 minutes. In a specific example, the cardioprotective pacing sequence initiated before the ischemic event includes 3 cycles of alternating pacing and non-pacing periods each being approximately 5-minute long. In one embodiment, the cardioprotective pacing sequence is initiated during the ischemic event and includes approximately 1 to 4 cycles of alternating pacing and non-pacing periods. The pacing period is in a range of approximately 30 seconds to 20 minutes. The non-pacing period is in a range of approximately 30 seconds to 20 minutes. In a specific example, the cardioprotective pacing sequence delivered during the ischemic event includes 3 cycles of alternating pacing and non-pacing periods each being approximately 5-minute long. In one embodiment, the cardioprotective pacing sequence is initiated after the ischemic event and includes approximately 1 to 4 cycles of alternating pacing and non-pacing periods. The pacing period is in a range of approximately 10 seconds to one minute. The non-pacing period is in a range of approximately 10 seconds to one minute. In one specific example, the cardioprotective pacing sequence delivered after the ischemic event includes 2 to 4 cycles of alternating pacing and non-pacing periods each being approximately 30-second long.

In various other embodiments, the cardioprotective pacing sequence includes pacing at one or more atrial tracking or other pacing modes. Examples of pacing modes used in such a cardioprotective pacing sequence include VDD, VVI, and DDD modes. In various embodiments, the VVI and DDD modes are delivered with a lower rate limit higher than the patient's intrinsic heart rate. In one embodiment, pacing therapy is delivered with pacing mode and/or other pacing parameters selected to create or augment mechanical stress on the myocardium or particular regions of the myocardium. In another embodiment, pacing therapy is delivered to prevent restenosis. In another embodiment, pacing therapy is delivered to treat an arrhythmia during the revascularization procedure, for example, when the patient experiences bradycardia during the procedure.

In various embodiments, during the pacing periods, the delivery of the pacing pulse is controlled according to a stress augmentation pacing mode, and during the non-pacing periods of the cardioprotective pacing sequence, no pacing pulse is timed to be delivered according to a non-pacing mode. When a pacing pulse is timed to be delivered, it will be delivered unless inhibited by an inhibitory event such as a detected intrinsic cardiac depolarization occurring before the scheduled delivery of the pacing pulse during a cardiac cycle. Under the non-pacing mode according to which no pacing pulse is timed to be delivered, the non-delivery is due to programming rather than inhibition by a detected inhibitory event. Under the stress augmentation pacing mode, pacing pulses are delivered to augment mechanical stress on the myocardium of the heart to a level effecting cardioprotection against myocardial injury. In various embodiments, the stress augmentation pacing mode is a standard or non-standard pacing mode with pacing parameter values selected for the desired level of myocardial stress augmentation according to the patients' needs, conditions, and responses. Examples of the stress augmentation pacing mode includes an atrial tracking pacing mode with a relatively short atrioventricular (AV) delay, a bradycardia pacing mode with a pacing rate substantially higher than the patient's intrinsic heart rate, and an asynchronous pacing mode with a pacing rate substantially higher than the patient's intrinsic heart rate.

In one embodiment, the pacing pulses are delivered according to the cardioprotective pacing protocol through PTVI device 110 during the revascularization procedure. After the revascularization procedure, if an implantable pacemaker is implanted into the patient, pacing therapy is delivered to heart 101 through one or more implantable leads from the implantable pacemaker. The pacing therapy includes delivering pacing pulses according to a pacing sequence that is substantially identical or similar to the cardioprotective pacing sequence applied during the revascularization procedure. The pacing sequence is delivered according to a predetermined schedule, such as on a predetermined periodic basis. This prevents or reduces possible cardiac injury after the revascularization, including cardiac injury and occurrences of arrhythmia caused by ischemic events including myocardial infarction that may be experienced by the patient after the implantation of the implantable pacemaker.

PTVI Device with Pacing Electrode(s)

Figure 4:
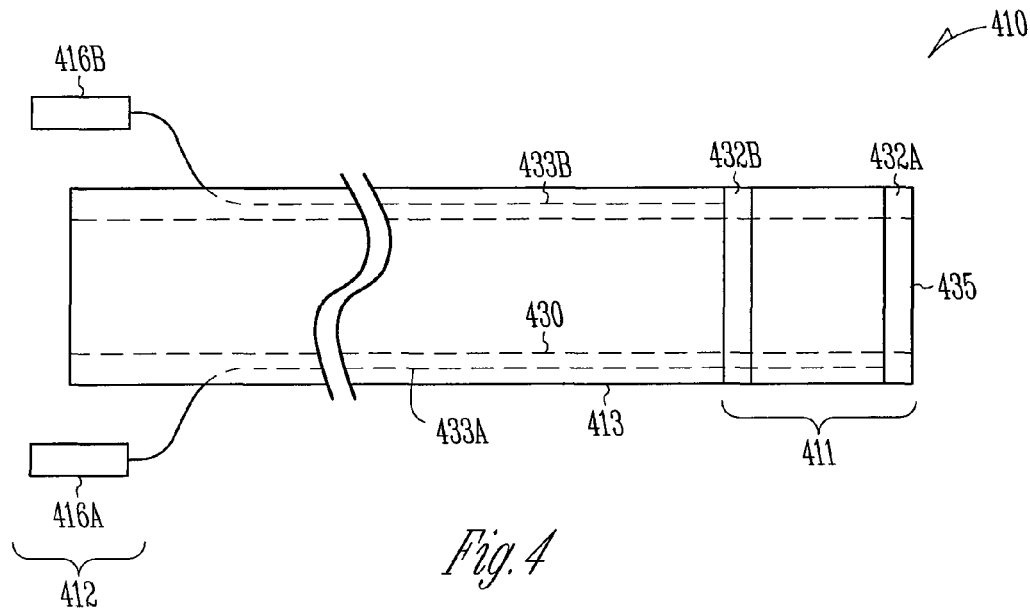
FIG. 4 is an illustration of an embodiment of a guide catheter with pacing electrodes.
Figure 5:
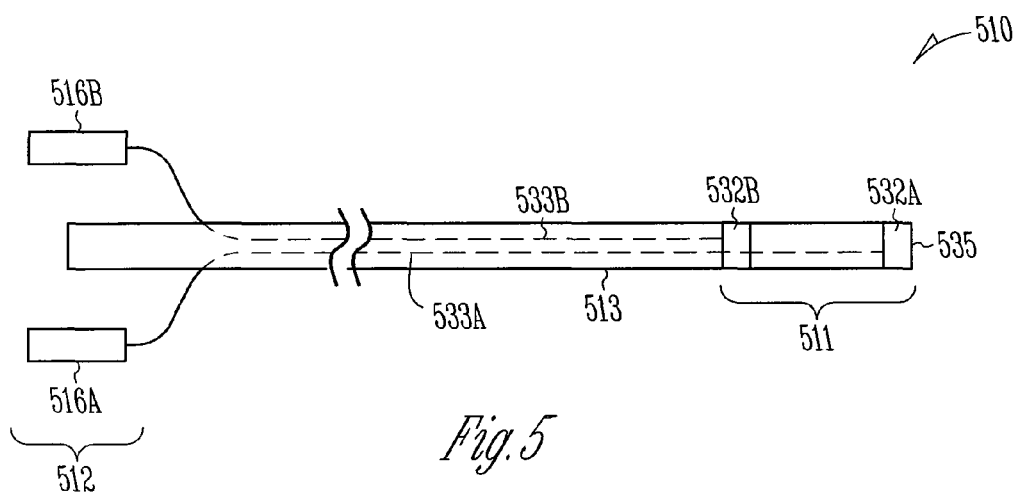
FIG. 5 is an illustration of an embodiment of a guide wire with pacing electrodes.
Figure 6:
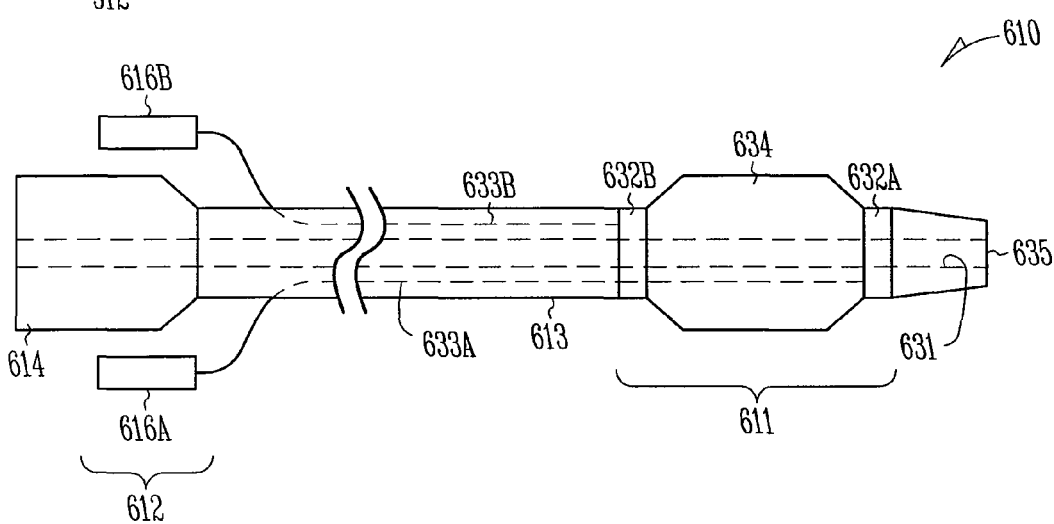
FIG. 6 is an illustration of an embodiment of an angioplasty catheter with pacing electrodes.

FIGS. 4-6 illustrate a PTVI device assembly that includes a guide catheter, a guide wire, and an angioplasty catheter. During a revascularization procedure such as a PTCA procedure, the guide catheter is inserted into the patient first, followed by the guide wire through a lumen of the guide catheter. The angioplasty catheter includes a lumen that accommodates a portion of the guide wire, thereby allowing the angioplasty catheter to be inserted into the patient through the guide catheter and over the guide wire. The guide catheter, guide wire, and angioplasty catheter are inserted in such a way that allows an angioplasty device, such as a balloon, of the angioplasty catheter to be placed in the portion of a blocked blood vessel that is to be reopened during the revascularization procedure.

FIG. 4 is an illustration of an embodiment of a guide catheter 410. Guide catheter 410 is an embodiment of PTVI device 110 and has an elongate shaft 413 between a distal end portion 411 and a proximal end portion 412. Distal end portion 411 is configured for intravascular placement and includes a distal tip 435. A lumen 430 extends within shaft 413 and has a proximal opening in proximal end portion 412 and a distal opening at distal tip 435. Lumen 430 accommodates at least a portion of the angioplasty catheter. Distal end portion 411 includes pacing electrodes 432A-B. In the illustrated embodiment, electrode 432A is incorporated onto distal tip 435. Conductor 433A is connected between pacing electrode 432A and a connector 416A. Conductor 433B is connected between pacing electrode 432B and a connector 416B. Connectors 416A-B are each part of proximal end portion 412. In one embodiment, conductors 433A-B each extend longitudinally within shaft 413. In another embodiment, conductors 433A-B each extend longitudinally on the outer surface of shaft 413 and are insulated.

In one embodiment, guide catheter 410 has a length in a range of approximately 50 cm to 150 cm. Shaft 413 has an outer diameter in a range of approximately 0.5 mm to 8 mm, and lumen 430 has a diameter in a range of approximately 0.4 mm to 7 mm. Conductors 433A-B are made of a metallic material such as stainless steel or an alloy of nickel, titanium, cobalt, gold, and/or silver chloride. Elongate shaft 413 is made of a material such as silicone, polyurethane, Teflon, or polytetrafluoroethylene (PTFE). Electrodes 432A-B are made of a metallic material such as platinum or an iridium alloy.

FIG. 5 is an illustration of an embodiment of a guide wire 510. Guide wire 510 is an embodiment of PTVI device 110 and has an elongate shaft 513 between a distal end portion 511 and a proximal end portion 512. Distal end portion 511 is configured for intravascular placement and includes a distal tip 535. Distal end portion 511 includes pacing electrodes 532A-B. In the illustrated embodiment, electrode 532A is incorporated onto distal tip 535. Conductor 533A is connected between pacing electrode 532A and a connector 516A. Conductor 533B is connected between pacing electrode 532B and a connector 516B. Connectors 516A-B are each part of proximal end portion 512. In one embodiment, conductors 533A-B each extend longitudinally within shaft 513. In another embodiment, conductors 533A-B each extend longitudinally on the outer surface of shaft 513 and are insulated. In one embodiment, one of connectors 533A-B is the core of guide wire 510.

In one embodiment, guide wire 510 has a length in a range of approximately 30 cm to 300 cm. Shaft 513 is an elongate cylindrical shaft having a diameter in a range of approximately 0.2 mm to 1.5 mm. Conductors 533A-B are made of a metallic material such as stainless steel or an alloy of nickel, titanium, and/or cobalt. Elongate shaft 513 is made of a material such as silicone, polyurethane, Teflon, or polytetrafluoroethylene (PTFE). Electrodes 532A-B are made of a metallic material such as platinum, an iridium alloy, gold, or silver chloride.

FIG. 6 is an illustration of an embodiment of an angioplasty catheter 610. Angioplasty catheter 610 is an embodiment of PTVI device 110 and has an elongate shaft 613 between a distal end portion 611 and a proximal end portion 612. A lumen 631 longitudinally extends within shaft 613 to accommodate at least a portion of a guide wire such as guide wire 510. Distal end portion 611 is configured for intravascular placement and includes a distal tip 635 and an angioplasty device 634. Angioplasty device 634 has one end approximately adjacent to distal tip 635 and another end coupled to shaft 613. In one embodiment, angioplasty device 634 includes an adjustable portion that has controllable expandability and contractibility. In the illustrated embodiment, angioplasty device 634 includes a balloon that is inflated and deflated through a lumen longitudinally extending within shaft 613 and connected between the chamber of the balloon and a connector 614 at proximal end portion 612. The balloon is inflatable using an air or liquid pump connected to that connector. In various embodiments, angioplasty device 634 includes a balloon or other device that allows for application of an angioplasty therapy such as vascular dilatation, stent delivery, brachytherapy (radiotherapy), atherectomy, or embolic protection. In one embodiment, distal tip 635 is a tapered tip that facilitates the insertion of angioplasty catheter 610 into a blood vessel. Distal end portion 611 includes pacing electrodes 632A-B. In the illustrated embodiment, pacing electrode 632A is approximately adjacent to one end of angioplasty device 634, and pacing electrode 632B is approximately adjacent to the other end of angioplasty device 634. A conductor 633A extends longitudinally within shaft 613 and is connected between pacing electrode 632A and a pacing connector 616A, which is part of proximal end portion 612. A conductor 633B extends longitudinally within elongate shaft 613 and is connected between pacing electrode 632B and a pacing connector 616B, which is also part of proximal end portion 612. In an alternative embodiment, pacing connectors 616A-B are physically integrated into one multi-conductor connector. Proximal end portion 612 also includes a proximal end device 614. In various embodiments, connector 614 includes a structure that accommodates all the mechanical connection and access requirements for angioplasty catheter 610, which depend on the function of angioplasty device 634. In one embodiment, connector 614 includes an integrated device. In another embodiment, connector 614 branches out into multiple connectors and/or other devices.

In one embodiment, angioplasty catheter 610 has a length in a range of approximately 50 cm to 150 cm. Shaft 613 is an elongate cylindrical shaft having a diameter in a range of approximately 1 mm to 5 mm. In one embodiment, angioplasty device 634 has an adjustable, substantially cylindrical or semi-spherical shape with a maximum diameter in a range of approximately 1 mm to 10 mm when fully expanded and a maximum diameter in a range of approximately 0.5 mm to 5 mm when fully contracted. In one embodiment, conductors 633A-B are each made of a metallic material such as stainless steel or an alloy of nickel, titanium, and/or cobalt. Electrodes 632A-B are each made of a metallic material such as platinum or an iridium alloy. Elongate shaft 613 has a tubular outer shell made of a material such as silicone, polyurethane, Teflon, or polytetrafluoroethylene (PTFE).

Guide catheter 410, guide wire 510, and angioplasty device 610 are illustrated in FIGS. 4-6 for illustrative but not restrictive purposes. For example, one or more pacing electrodes can be distributed on each of these PTVI devices in any way allowing delivery of pacing pulses to desirable locations. In various embodiments, one or more pacing electrodes are incorporated onto one or more of guide catheter 410, guide wire 510, and angioplasty device 610 for delivering pacing pulses through the PTVI device assembly including these three devices. In one embodiment, one or more defibrillation electrodes are also incorporated onto one or more of guide catheter 410, guide wire 510, and angioplasty device 610 for delivering defibrillation shocks through the PTVI device assembly. In one embodiment, one or more pacing electrodes such as one of more of pacing electrodes 432A-B, 532A-B, and 632A-B are made of conductive radiopaque material to function as one or more radiopaque markers for locating guide catheter 410, guide wire 510, and/or angioplasty device 610 using fluoroscopy.

In one embodiment, angioplasty device 610 includes a balloon. Guide wire 510 remains within lumen 631 when the balloon is inflated. The inflated balloon is over pacing electrodes 532A-B. When being deflated, the balloon is retracted to expose electrodes 532A-B, thereby allowing delivery of pacing pulses. In one embodiment, shaft 613 includes a portion having an adjustable length that is shortened to expose electrodes 532A-B when the balloon is deflated.

In one application during a PTCA procedure for reopening, for example, right coronary artery 107, guide catheter 410 is inserted into femoral artery 104 and advanced to aorta 106 until distal tip 435 reaches the point where right coronary artery 107 branches from aorta 106. Guide wire 510 is introduced through lumen 430 of guide catheter 410 until distal end 535 is in right coronary artery 107. Angioplasty catheter 610 is then introduced through lumen 430 over guide wire 510 until angioplasty device 634 (balloon) is in the portion of right coronary artery 107. In one embodiment, the acute pacing cardioprotection therapy is delivered using electrodes 432A-B as soon as guide catheter 410 is in place for the PTCA procedure. In one embodiment, when the PTVI device assembly including guide catheter 410, guide wire 510, and angioplasty device 610 are in place for the PTCA procedure, the acute pacing cardioprotection therapy is delivered using one or more pairs of pacing electrodes selected from electrodes 432A-B, 532A-B, 632A-B, and 119.

In one embodiment, the PTVI device assembly allows for combined pacing cardioprotection therapy and ischemic cardioprotection therapy. For example, the ischemic cardioprotection therapy is applied by intermittently occluding a blocked vessel by inflating and deflating angioplasty device 634 (balloon) of angioplasty catheter 610, in addition to delivering the pacing cardioprotection therapy through the one or more pairs of pacing electrodes.

Various embodiments of the PTVI devices and the pacemaker are discussed below as examples illustrating the pacing system for delivering the acute pacing cardioprotection therapy during a revascularization procedure. In general, such a pacing system includes a pacemaker capable of delivering pacing pulses according to a cardioprotective pacing protocol, such as discussed above with reference to FIG. 3, and one or more PTVI devices each including one or more pacing electrodes. In one embodiment, the one or more PTVI devices includes devices used to perform the revascularization procedure, such as guide catheters, guide wires, and angioplasty catheters, that are modified to allow delivery of the acute pacing cardioprotection therapy. In another embodiment, the one or more PTVI devices includes one or more devices that are not required to perform the revascularization procedure itself but configured to allow delivery of pacing pulses during the revascularization procedure. In various embodiments, the PTVI devices have sizes identical or similar to those discussed above, and are constructed using materials identical or similar to those discussed above.

FIGS. 7-13 illustrate several specific embodiments of guide catheter 410, guide wire 510, and angioplasty device 610. In various embodiments, pacing pulses are delivered during a revascularization procedure using any PVTI device with at least one pacing electrode, alone or in combination with any other PTVI device(s) each with at least one pacing electrode and/or electrode(s) placed in or on the patient receiving the revascularization procedure.

Figure 7:
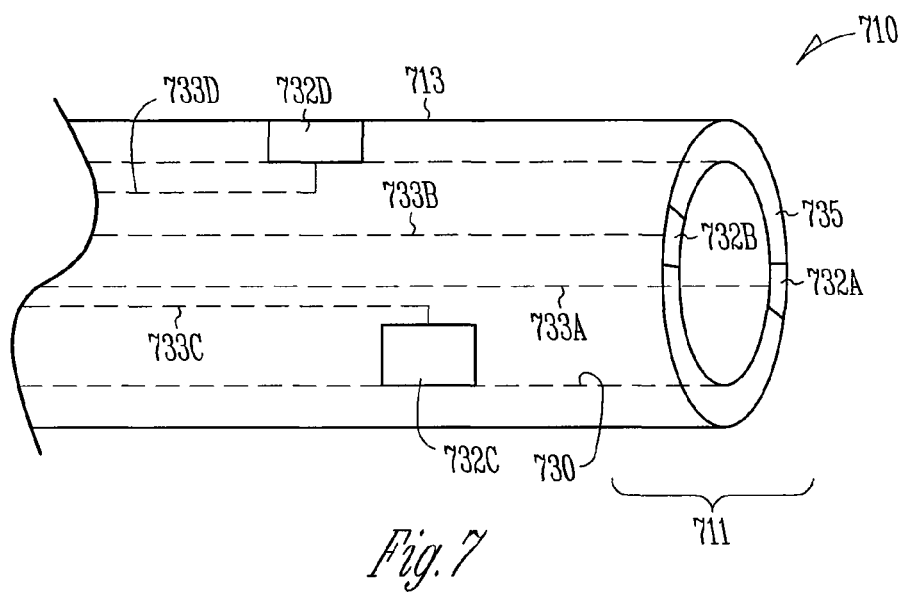
FIG. 7 is an illustration of an embodiment of a distal portion of the guide catheter with pacing electrodes.

FIG. 7 is an illustration of an embodiment of a distal portion of a guide catheter 710 showing its distal end portion 711 and elongate shaft 713. Guide catheter 710 is another embodiment of guide catheter 410. As shown in FIG. 7, distal end portion 711 includes a distal tip 735 where a lumen 730 ends with its distal opening. Lumen 730 is configured to accommodate at least a portion of an angioplasty catheter such as angioplasty catheter 610 and allow the angioplasty device of the angioplasty catheter to exit from guide catheter 710. Pacing electrodes 732A-B are incorporated onto distal tip 735, adjacent to the distal opening of lumen 730. Pacing electrodes 732C-D are incorporated onto shaft 713. Conductors 733A-D provide for electrical connections allowing pacing pulses to be delivered to pacing electrodes 732A-D when the pacemaker is connected to the proximal end of guide catheter 710. In various other embodiments, guide catheter 710 includes any number of pacing electrodes incorporated onto distal end portion 711 and/or shaft 713. In various embodiments, any one or more of the pacing electrodes incorporated onto guide catheter 710 are selected for delivering the pacing pulses during a revascularization procedure.

Figure 8:
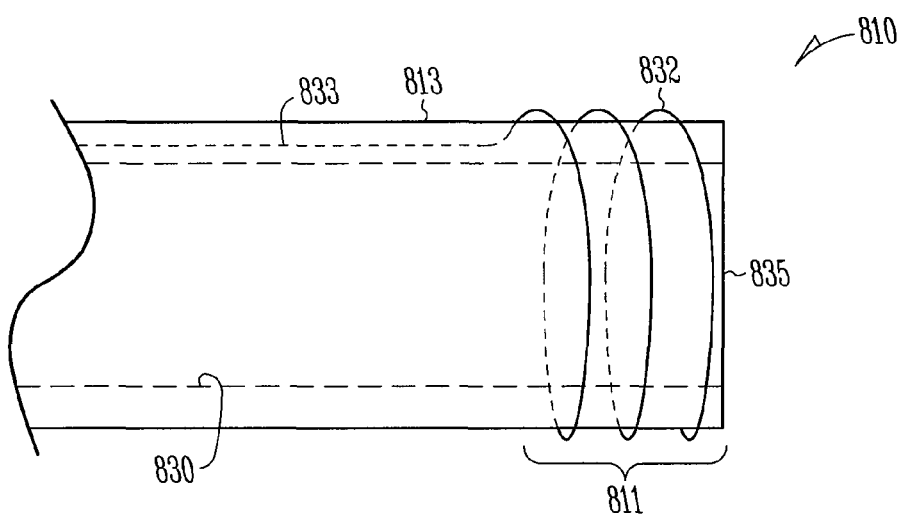
FIG. 8 is an illustration of another embodiment of a distal portion of the guide catheter with pacing electrodes.

FIG. 8 is an illustration of an embodiment of a distal end portion of a guide catheter 810 showing its distal end portion 811 and elongate shaft 813. Guide catheter 810 is another embodiment of guide catheter 410. As shown in FIG. 8, distal end portion 811 includes a distal tip 835 where a lumen 830 ends with its distal opening. Lumen 830 is configured to accommodate at least a portion of an angioplasty catheter such as angioplasty catheter 610 and allow the angioplasty device of the angioplasty catheter to exit from guide catheter 810. A pacing electrode 832 configured as a coil electrode is incorporated onto distal end portion 811 near distal tip 835. A conductor 833 provides for electrical connection allowing pacing pulses to be delivered to pacing electrode 832 when the pacemaker is connected to the proximal end of guide catheter 810. In various other embodiments, guide catheter 810 includes any number of coil electrodes incorporated onto distal end portion 811 and/or shaft 813. In various embodiments, any one or more coil electrodes incorporated onto guide catheter 810 are selected for delivering the pacing pulses during a revascularization procedure.

Figure 9:
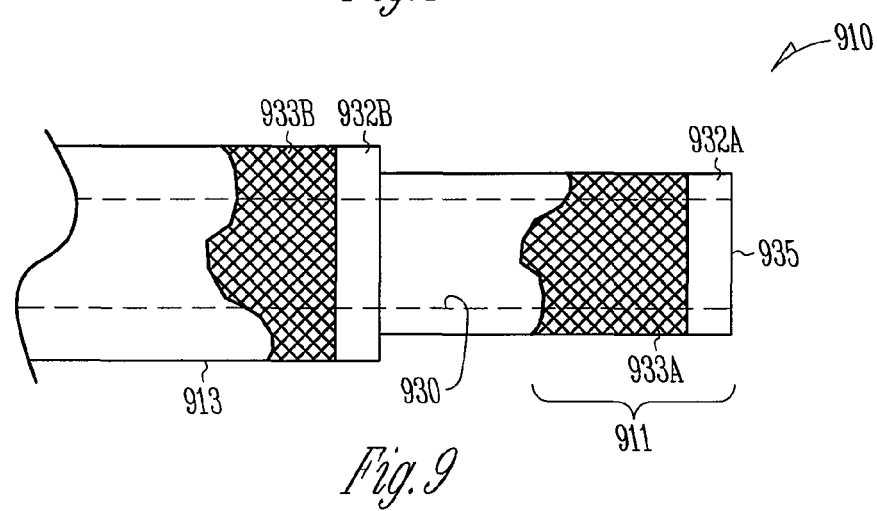
FIG. 9 is an illustration of another embodiment of a distal portion of the guide catheter with pacing electrodes.

FIG. 9 is an illustration of an embodiment of the distal portion of a guide catheter 910 showing its distal end portion 911 and elongate shaft 913. Guide catheter 910 is another embodiment of guide catheter 410. As shown in FIG. 9, distal end portion 911 includes a distal tip 935 where a lumen 930 ends with its distal opening. Lumen 930 is configured to accommodate at least a portion of an angioplasty catheter such as angioplasty catheter 610 and allow the angioplasty device of the angioplasty catheter to exit from guide catheter 910. A pacing electrode 932A is configured as a collar electrode and incorporated onto distal tip 935. Another pacing electrode 932B is configured as another collar electrode and incorporated onto shaft 913. Two layers of tubular metal braid each extend within guide catheter 910 and connect to one of pacing electrodes 932A-B. These two layers of tubular metal braid function as conductors 933A-B, which provide for electrical connections allowing pacing pulses to be delivered to pacing electrodes 932A-B when the pacemaker is connected to the proximal end of guide catheter 910. In various other embodiments, guide catheter 910 includes any number of collar electrodes incorporated onto distal end portion 911 and/or shaft 913. In various embodiments, any one or more collar electrodes incorporated onto guide catheter 910 are selected for delivering the pacing pulses during a revascularization procedure.

Figure 10:
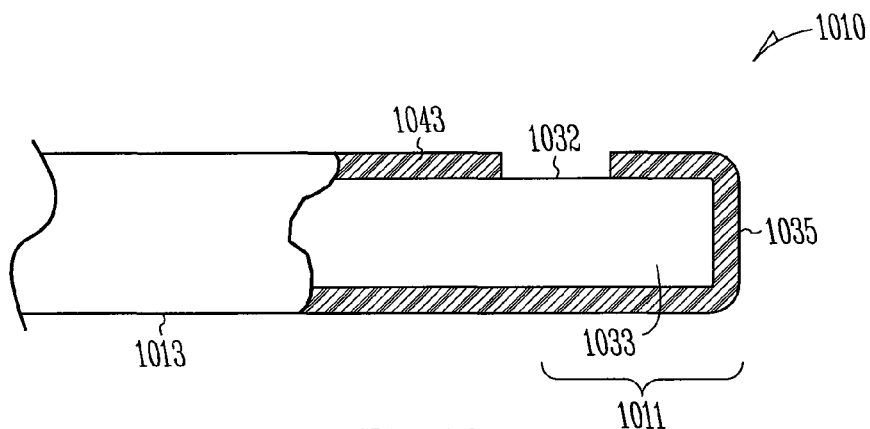
FIG. 10 is an illustration of an embodiment of a distal portion of the guide wire with pacing electrodes.

FIG. 10 is an illustration of an embodiment of the distal portion of a guide wire 1010 showing its distal end portion 1011 and elongate shaft 1013. Guide wire 1010 is another embodiment of guide wire 510 and is formed by a conductor 1033 covered by an insulation layer 1043. In the illustrated embodiment, distal end portion 1011 includes a distal tip 1035 and a pacing electrode 1032 formed by an opening in insulation layer 1043 that exposes a portion of conductor 1033. Pacing pulses are delivered through conductor 1033 to the patient through opening/electrode 1032 when the pacemaker is connected to the proximal end of guide wire 1010. In various other embodiments, insulation layer 1043 includes any number of openings functioning as electrodes on distal end portion 1011 and/or shaft 1013.

Figure 11:
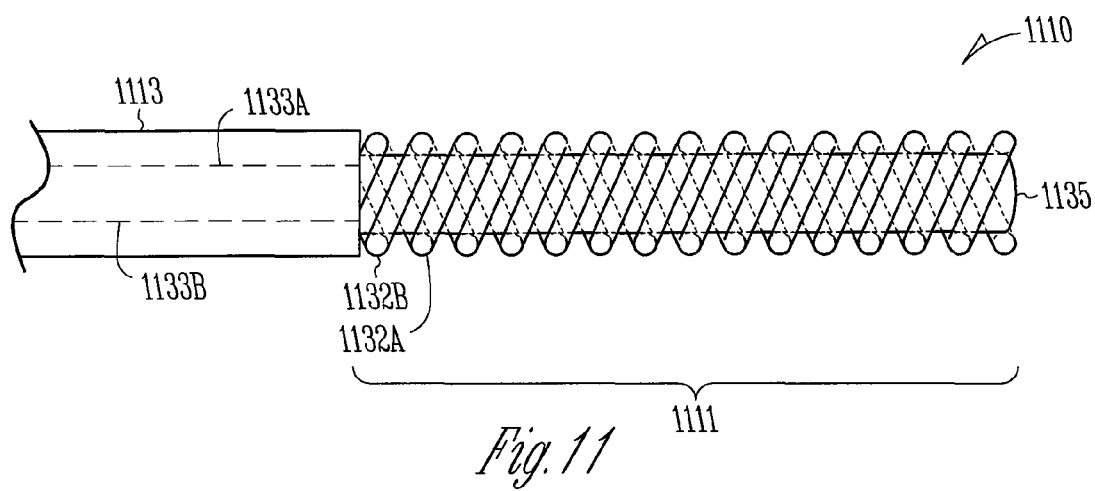
FIG. 11 is an illustration of another embodiment of a distal portion of the guide wire with pacing electrodes.

FIG. 11 is an illustration of an embodiment of the distal portion of a guide wire 1110 showing its distal end portion 1111 and elongate shaft 1113. Guide wire 1110 is another embodiment of guide wire 510 and is formed by a plurality of conductors covered by an insulation layer. In the illustrated embodiment, guide wire 1110 includes conductors 1133A-B that are insulated to form shaft 1113 and exposed to form pacing electrodes 1132A-B at distal end portion 1111. Pacing electrodes 1132A-B include exposed portions of conductors 1133A-B in a helical form extending to a distal tip 1135 of guide wire 1110. In one embodiment, pacing electrodes 1132A-B are separated from each other to be used as an anode and a cathode for delivering the pacing pulses when the pacemaker is connected to the proximal end of guide wire 1110. In various other embodiments, guide wire 1110 includes one, two, or more than two conductors with their distal end portions exposed and configured to function as one, two, or more electrically separated pacing electrodes.

Figure 12:
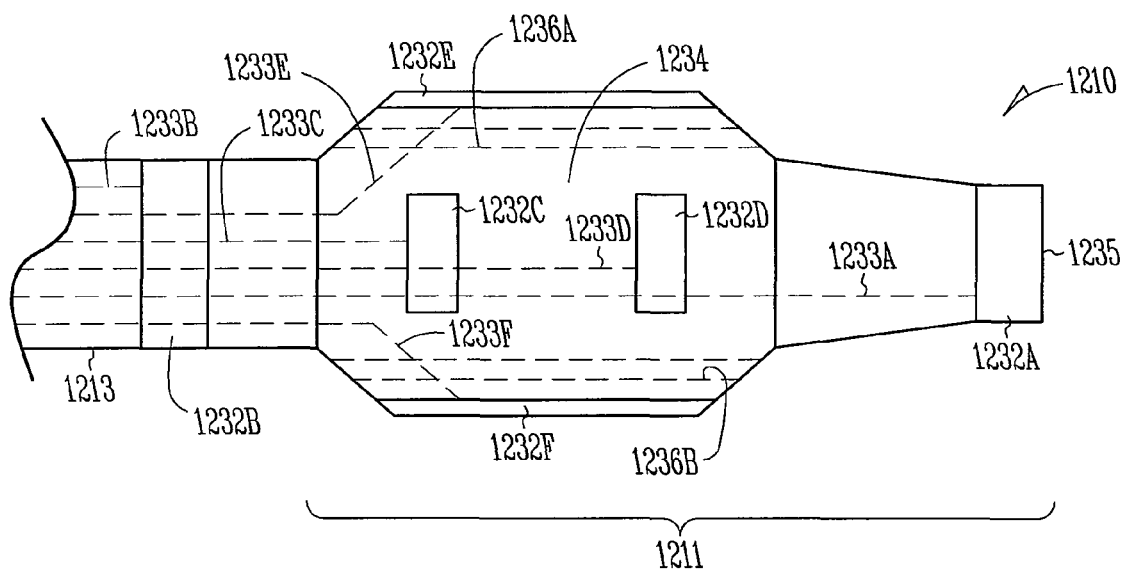
FIG. 12 is an illustration of an embodiment of a distal portion of the angioplasty catheter with a balloon and pacing electrodes.

FIG. 12 is an illustration of an embodiment of the distal portion of an angioplasty catheter 1210. Angioplasty catheter 1210 is another embodiment of angioplasty catheter 610. Distal end portion 1211 includes a balloon 1234 coupled between a distal tip 1235 and an elongate shaft 1213. In the illustrated embodiment, balloon 1234 includes perfusion channels 1236A-B and cutting blades 1232E-F. Perfusion channels 1236A-B each include a lumen having a proximal opening and a distal opening to allow blood to flow through balloon 1234 when it is inflated. In one embodiment, when balloon 1234 is inflated, the lumen has a diameter that allows the distal end portion of a pacing lead to enter its proximal opening and exit from its distal opening such that one or more pacing electrodes of the pacing lead are placed distal to the lumen. Cutting blades 1232E-F cut plaques in a blood vessel as balloon 1234 is being inflated in that blood vessel. In one embodiment, cutting blades 1232E-F are each made of metal and used as a pacing electrode. In various embodiments, balloon 1234 is a perfusion balloon including one or more perfusion channels and/or a cutting balloon including one or more cutting blades. Angioplasty catheter 1210 also includes pacing electrodes 1232A-D. Pacing electrode 1232A is incorporated onto distal tip 1235. Pacing electrode 1232B is incorporated onto shaft 1213. Pacing electrodes 1232C-D are incorporated onto balloon 1234. In one embodiment, one or more of pacing electrodes 1232A-D are made of radiopaque material to function as one or more radiopaque markers for locating distal end portion 1211 using fluoroscopy. Conductors 1233A-F provide for electrical connections allowing pacing pulses to be delivered to pacing electrodes 1232A-F when the pacemaker is connected to the proximal end of angioplasty catheter 1210. In the illustrated embodiment, angioplasty catheter 1210 includes pacing electrodes 1232A-F. In various embodiments, angioplasty catheter 1210 includes any one or more of pacing electrodes 1232A-F as well as other one or more pacing electrodes incorporated onto distal end portion 1211 and/or shaft 1213. In various embodiments, any one or more pacing electrodes incorporated onto angioplasty catheter 1210 are selected for delivering the pacing pulses during a revascularization procedure.

A potential advantage for using one or more of pacing electrodes 1232C-F for delivering pacing pulses is that when balloon 1234 is inflated, the pacing electrodes are pressed onto the vascular wall to form stable electrical contacts. In one embodiment, a pacing lead that is substantially identical or similar to guide wire 510 is introduced along the side of angioplasty catheter 1210, with its one or more pacing electrodes placed over balloon 1234 such that when balloon 1234 is inflated, the one or more pacing electrodes of that pacing lead is securely pressed onto the vascular wall to form a stable electrical contact for delivering pacing pulses.

Figure 13:
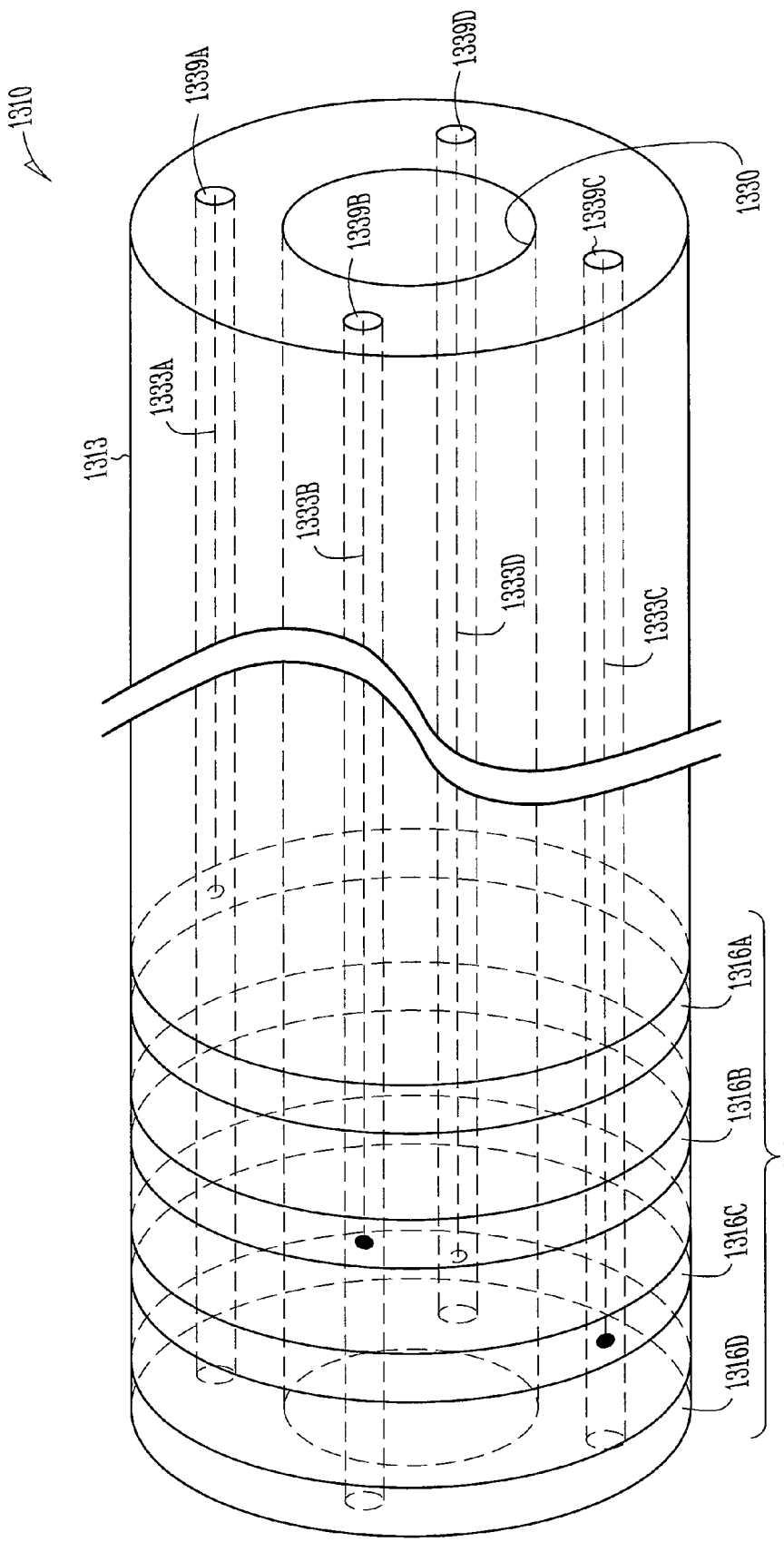
FIG. 13 is an illustration of an embodiment of a proximal portion of the angioplasty catheter with pacing electrodes.

FIG. 13 is an illustration of an embodiment of the proximal portion of an angioplasty catheter 1310 showing a proximal end portion 1312 and an elongate shaft 1313. In the illustrated embodiment, angioplasty catheter 1310 includes conductors 1333A-D connected between ring connectors 1316A-D in proximal end portion 1312 and pacing electrodes in the distal end portion of angioplasty catheter 1310. In various embodiments, angioplasty catheter 1310 includes one or more conductors and ring connectors, depending on the number of pacing electrodes. A lumen 1330 extends longitudinally within angioplasty catheter 1310 to accommodate a guide wire such as guide wire 510 and/or to allow inflation and deflation of a balloon at the distal end portion. Lumens 1339A-D each accommodates one of conductors 1333A-D.

FIGS. 14-37 illustrate various specific examples of PTVI devices that include pacing electrodes to allow an acute pacing cardioprotection therapy to be delivered during a revascularization procedure. In various embodiments, each of these PTVI devices may function as one of the guide catheter, guide wire, and angioplasty catheter as discussed above, or a PTVI pacing device that is otherwise not required for the revascularization procedure. In various embodiments, pacing pulses are delivered from an external pacemaker connected to one or more PTVI devices with pacing electrodes, or from a pacemaker incorporated onto a PTVI device.

Example: Pacing Catheter with Expandable Distal End

FIGS. 14-18 illustrate various embodiments of a pacing catheter including an expandable distal end including one or more pacing electrodes. When expanded in a blood vessel during a revascularization procedure, the distal end is stabilized in the blood vessel to provide reliable electrical contact(s) between the one or more pacing electrodes and the vascular wall for delivering pacing pulses.

Figure 14:
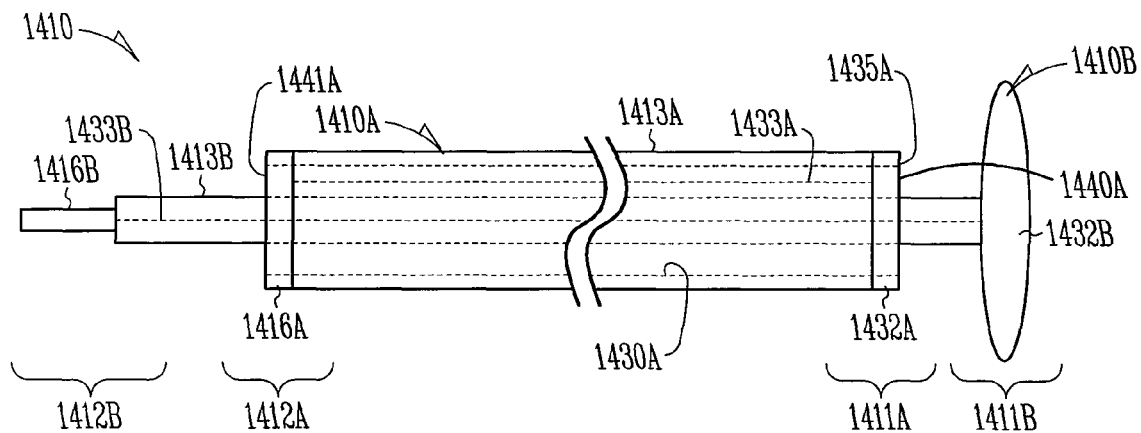
FIG. 14 is an illustration of an embodiment of a pacing catheter including a sheath and a pacing lead having an expandable distal end.

FIG. 14 is an illustration of an embodiment of a pacing catheter 1410. Pacing catheter 1410 is a PTVI device assembly including a sheath 1410A and a pacing lead 1410B. Sheath 1410A includes a sheath proximal end portion 1412A, a sheath distal end portion 1411A configured for intravascular placement and including a distal tip 1435A, an elongate sheath shaft 1413A coupled between proximal end portion 1412A and distal end portion 1411A, and a lumen 1430A. Lumen 1430A extends within shaft 1413A and has a proximal opening 1441A at proximal end portion 1412A and a distal opening 1440A at distal tip 1435A. In one embodiment, sheath 1410A is a guide catheter for use in a revascularization procedure. In the illustrated embodiment, sheath 1410A includes a pacing electrode 1432A incorporated onto distal end portion 1411A, a connector 1416A incorporated onto proximal end portion 1412A, and a conductor 1433A providing for electrical connection between pacing electrode 1432A and connector 1416A. In various other embodiments, sheath 1410A includes any number of pacing electrodes, or no pacing electrode.

Pacing lead 1410B includes a lead proximal end portion 1412B, an expandable lead distal end portion 1411B configured for intravascular placement, and an elongate lead shaft 1413B coupled between proximal end portion 1412B and distal end portion 1411B. Pacing lead 1410B is configured to allow distal end portion 1411B to enter lumen 1430A through proximal opening 1441A and exit from lumen 1430A through distal opening 1440A by being pushed into lumen 1430A, and retract into lumen 1430A through distal opening 1440A and exit lumen 1430A from proximal opening 1441A by being pulled from lumen 1430A. Distal end portion 1411B includes a pacing electrode 1432B. Pacing lead 1410B includes a connector 1416B electrically connected to pacing electrode 1432B via a conductor 1433B extending through shaft 1413B. In one embodiment, pacing electrode 1432B is incorporated onto distal end portion 1411B. In another embodiment, pacing electrode 1432B includes the entire distal end portion 1411B or a substantial portion thereof. Distal end portion 1411B is in a contracted state while being placed in lumen 1430A and in an expanded state after exiting from lumen 1430A. In one embodiment, distal end portion 1411B expands upon exiting from lumen 1430A and contracts upon retracting into lumen 1430A. In one embodiment, distal end portion 1411B is self-expandable and is in an expanded state when not being restrained. When being placed in a blood vessel and in its expanded state, distal end portion 1411B provides for a stable electrical contact between pacing electrode 1432B and the vascular wall for delivering pacing pulses.

Figure 15:
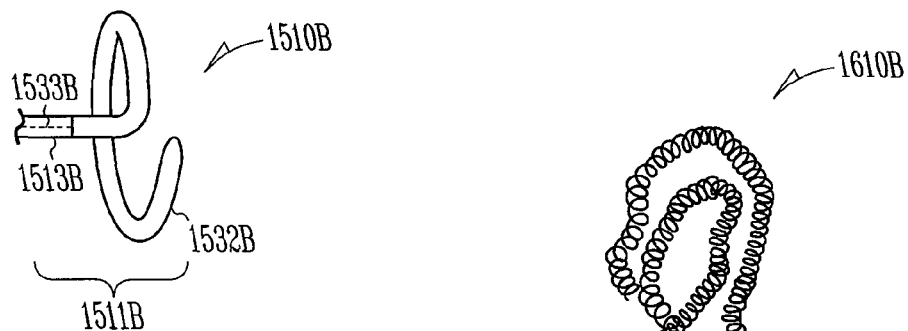
FIG. 15 is an illustration of an embodiment of the distal end portion of a pacing lead of the pacing catheter of FIG. 14.
Figure 16:
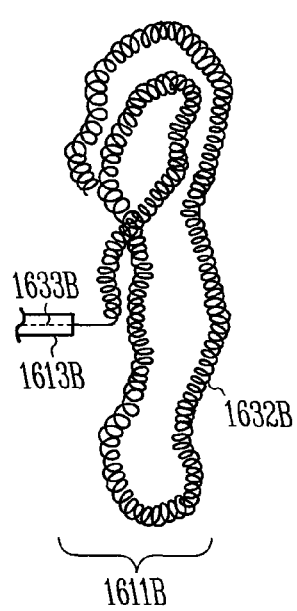
FIG. 16 is an illustration of another embodiment of the distal end portion of a pacing lead of the pacing catheter of FIG. 14.
Figure 17:
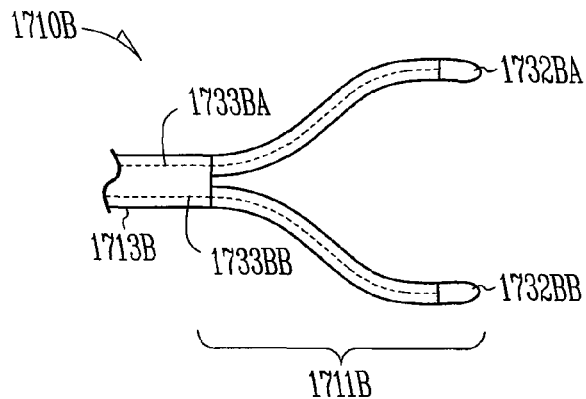
FIG. 17 is an illustration of another embodiment of the distal end portion of a pacing lead of the pacing catheter of FIG. 14.

In various embodiments, pacing lead 1410B includes one or more pacing electrodes, one or more connectors, and one or more conductors extending through shaft 1413B and connecting between one of the one or more pacing electrodes and one of the one or more connectors. FIGS. 15-17 illustrate various embodiments of distal end portion 1411B each including one or more pacing electrodes.

FIG. 15 is an illustration of an embodiment of a lead distal end portion 1511B of a pacing lead 1510B, which is another embodiment of pacing lead 1410B. Pacing lead 1510B includes a pacing electrode 1532B at distal end portion 1511B connected to a conductor 1533B extending in an elongate lead shaft 1513B. Pacing electrode 1532B is formed by a wire that springs into a coil upon exiting from lumen 1430A from distal opening 1440A. The coil has a diameter suitable for stabilizing lead distal end 1511B in a blood vessel.

FIG. 16 is an illustration of an embodiment of a lead distal end portion 1611B of a pacing lead 1610B, which is another embodiment of pacing lead 1410B. Pacing lead 1610B includes a pacing electrode 1632B at distal end portion 1611B connected to a conductor 1633B extending in an elongate lead shaft 1613B. Pacing electrode 1632B includes a Guglielmi Detachable Coil (GDC®). GDC is a coil made of memory material that is restrained during delivery into the body and expands when it is no longer restrained. The coil is electrically sensitive such that it is detached from its delivery device by passing a low-amplitude electrical current through the delivery device. Thus, pacing electrode 1632B expands upon exiting from lumen 1430A from distal opening 1440A and is disconnected from shaft 1613B after the delivery of the pacing pulses.

FIG. 17 is an illustration of an embodiment of a lead distal end portion 1711B of a pacing lead 1710B, which is another embodiment of pacing lead 1410B. In the illustrated embodiment, pacing lead 1710B includes pacing electrodes 1732BA and 1732BB at distal end portion 1711B connected to conductors 1733BA and 1733BB extending in an elongate lead shaft 1713B. Conductors 1733BA and 1733BB at distal end 1711B are substantially unbiased while being restrained in lumen 1430A and biased when distal end portion 1711B has exited from lumen 1430A from distal opening 1440A. The biased portion of conductors 1733BA and 1733BB are made of one or more memory materials and configured to be suitable for stabilizing distal end portion 1711B in a blood vessel when biased. In various embodiments, distal end portion 1711A includes a plurality of wires each being substantially unbiased when being restrained in lumen 1430A and biased when not being restrained. The plurality of wires forms one or more pacing electrodes.

Figure 18:
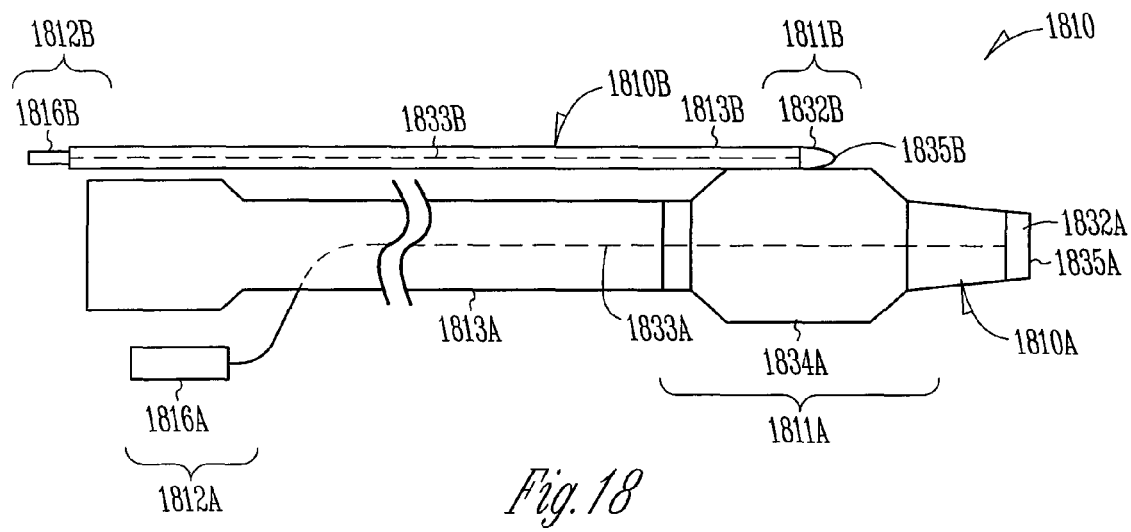
FIG. 18 is an illustration of an embodiment of a percutaneous transluminal vascular intervention (PTVI) device assembly including a pacing lead and a balloon catheter.

FIG. 18 is an illustration of an embodiment of a PTVI device assembly 1810 including a pacing lead 1810B and a balloon catheter 1810A. Balloon catheter 1810A is an angioplasty catheter including a catheter proximal end portion 1812A, a catheter distal end portion 1811A configured for intravascular placement and including a catheter distal tip 1835A and a balloon 1834A, an elongate catheter shaft 1813A between proximal end portion 1812A and distal end portion 1811A. A pacing electrode 1832A is incorporated onto distal tip 1835A. A conductor 1833A extends within shaft 1813A and provides for electrical connection between pacing electrode 1832A and a connector 1816A at proximal end portion 1812A.

Pacing lead 1810B includes a lead proximal end 1812B, a lead distal end 1811B including a distal tip 1835B, and an elongate lead shaft 1813B between proximal end portion 1812B and distal end portion 1811B. A pacing electrode 1832B is incorporated onto distal tip 1835B. A conductor 1833B extends within shaft 1813B and provides for electrical connection between pacing electrode 1832B and a connector 1816B at proximal end portion 1812B.

To deliver pacing pulses using pacing electrodes 1832A and 1832B, pacing lead 1810B is placed such that pacing electrode 1832B is over balloon 1834A when distal end portions 1811A and 1811B are positioned in the intended pacing site in a blood vessel. When balloon 1834A is inflated, pacing electrode 1832B is pressed by balloon 1834A onto the interior wall of the blood vessel to provide a stable electrical contact for delivering the pacing pulses. In one embodiment, PTVI device assembly 1810 allows for delivering combined ischemic cardioprotection therapy by inflating and deflating balloon 1834A and pacing cardioprotection therapy by delivering cardioprotective pacing via electrodes 1832A and 1832B.

Example: Pacing Catheter for Access to Multiple Vessels

Figure 19:
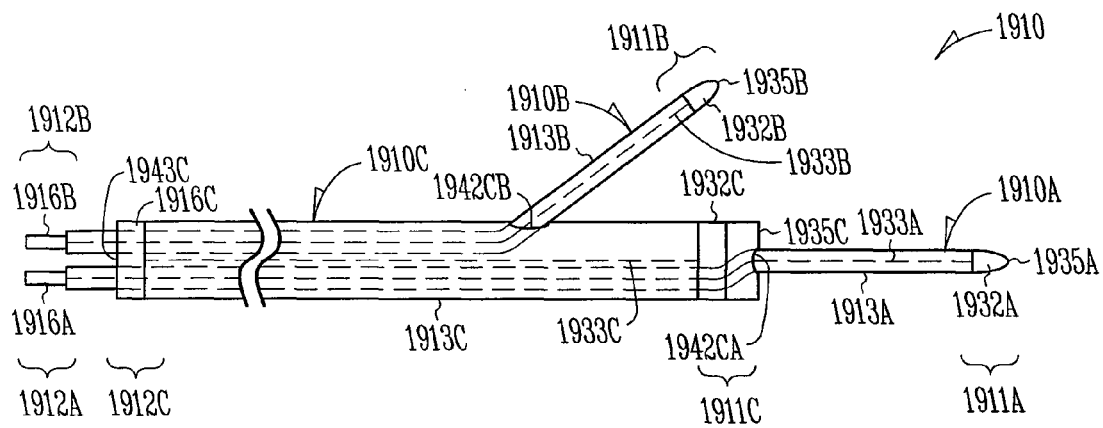
FIG. 19 is an illustration of an embodiment of a pacing catheter including multiple pacing leads for access to multiple blood vessels.
Figure 20:
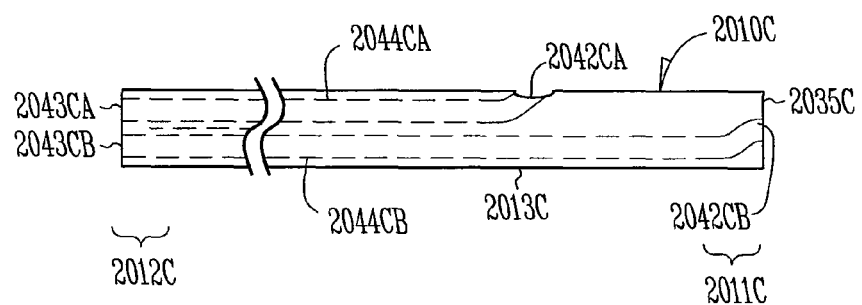
FIG. 20 is an illustration of an embodiment of a catheter of the pacing catheter of FIG. 19.

FIGS. 19 and 20 illustrate various embodiments of a pacing catheter through which multiple pacing leads are introduced into multiple blood vessels. The pacing catheter includes exit ports arranged according to the anatomy of a portion of the vascular system where the intended pacing sites are located, such that the pacing leads exit from the pacing catheter through the exit ports into the blood vessels in which the pacing electrodes are to be placed. For example, after the pacing catheter is inserted into a major blood vessel, such as the vessel to be reopened during a revascularization procedure, the pacing leads exit from the exit ports to enter the major blood vessel and/or one or more blood vessels branching from the major blood vessel.

FIG. 19 is an illustration of an embodiment of a pacing catheter 1910. Pacing catheter 1910 is a PTVI device assembly including multiple pacing leads for access to multiple vessels. In the illustrated embodiment, pacing catheter 1910 includes pacing leads 1910A and 1910B and a catheter 1910C.

Pacing lead 1910A includes a lead proximal end portion 1912A including a connector 1916A, a lead distal end portion 1911A configured for intravascular placement and including a lead distal tip 1935A, and an elongate lead shaft 1913A coupled between lead proximal end portion 1912A and lead distal end portion 1911A. A pacing electrode 1932A is incorporated onto distal tip 1935A. A connector 1933A provides for electrical connection between pacing electrode 1932A and connector 1916A.

Pacing lead 1910B includes a lead proximal end portion 1912B including a connector 1916B, a lead distal end portion 1911B configured for intravascular placement and including a lead distal tip 1935B, and an elongate lead shaft 1913B coupled between lead proximal end portion 1912B and lead distal end portion 1911B. A pacing electrode 1932B is incorporated onto distal tip 1935B. A connector 1933B provides for electrical connection between pacing electrode 1932B and connector 1916B.

Catheter 1910C includes a catheter proximal end portion 1912C including a connector 1916C, a catheter distal end portion 1911C configured for intravascular placement and including a catheter distal tip 1935C, and an elongate catheter shaft 1913C coupled between catheter proximal end portion 1912C and catheter distal end portion 1911C. A pacing electrode 1932C is incorporated onto distal tip 1935C. A connector 1933C provides for electrical connection between pacing electrode 1932C and connector 1916C. Catheter 1910C includes one or more entry ports 1943C at proximal end portion 1912C, exit port 1942CA at distal tip 1935C, and exit port 1942CB on shaft 1913C. To deliver pacing pulses, distal ends 1911A-B of pacing leads 1910A-B are inserted into catheter 1910C through entry port(s) 1943C and exit through exit ports 1942CA-B. Exit ports 1942CA-B are positioned to allow distal ends 1911A-B to enter two blood vessels where pacing electrodes 1932A-B are to be placed. In one embodiment, exit port 1942CA is positioned on catheter 1910C to allow pacing electrode 1932A to be placed in a main blood vessel into which catheter 1910C is placed, and pacing electrode 1932B is to be placed in another blood vessel branched from the main blood vessel.

In one application, exit ports 1942CA-B are positioned to allow distal end portions 1911A-B to enter the left anterior descending (LAD) coronary artery and the right coronary artery.

In various embodiments, PTVI device assembly 1910 includes two or more pacing leads that are introduced through catheter 1910C, which includes two or more exit ports each allow one of the pacing leads to exit into a blood vessel. Each of the two or more pacing leads includes one or more pacing electrodes.

FIG. 20 is an illustration of an embodiment of a catheter 2010C, which is an embodiment of catheter 1910C. Catheter 2010C includes a catheter proximal end portion 2012C, a catheter distal end portion 2011C configured for intravascular placement and including a catheter distal tip 2035C, and an elongate catheter shaft 2013C coupled between catheter proximal end portion 2012C and catheter distal end portion 2011C. Catheter 2010C includes entry ports 2043CA-B at proximal end portion 2012C, exit port 2042CB at distal tip 2035C, exit port 2042CA on shaft 2013C, and guiding channels 2044CA-B each including a lumen extending within a portion of shaft 2013C. Guiding channel 2044CA includes a lumen connecting entry port 2043CA and exit port 2042CA. Guiding channel 2044CB includes a lumen connecting entry port 2043CB and exit port 2042CB. To deliver the pacing pulses, pacing leads 1910A-B are each placed using one of guiding channel 2044CA-B, with the distal tip entering one of entry port 2043A-B and exiting from one of exit port 2042A-B.

Example: Pacing Catheter Releasing Conductive Liquid as Electrode

Figure 21:
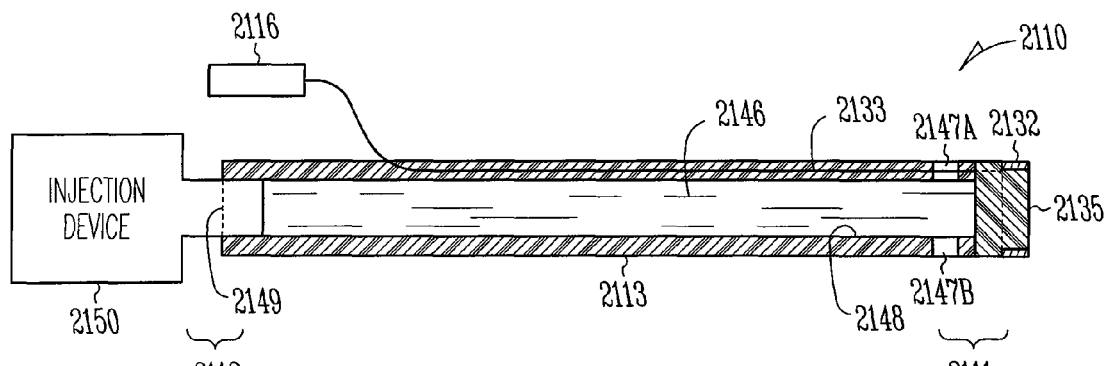
FIG. 21 is an illustration of an embodiment of a pacing catheter releasing conductive liquid and an injection device.
Figure 22:
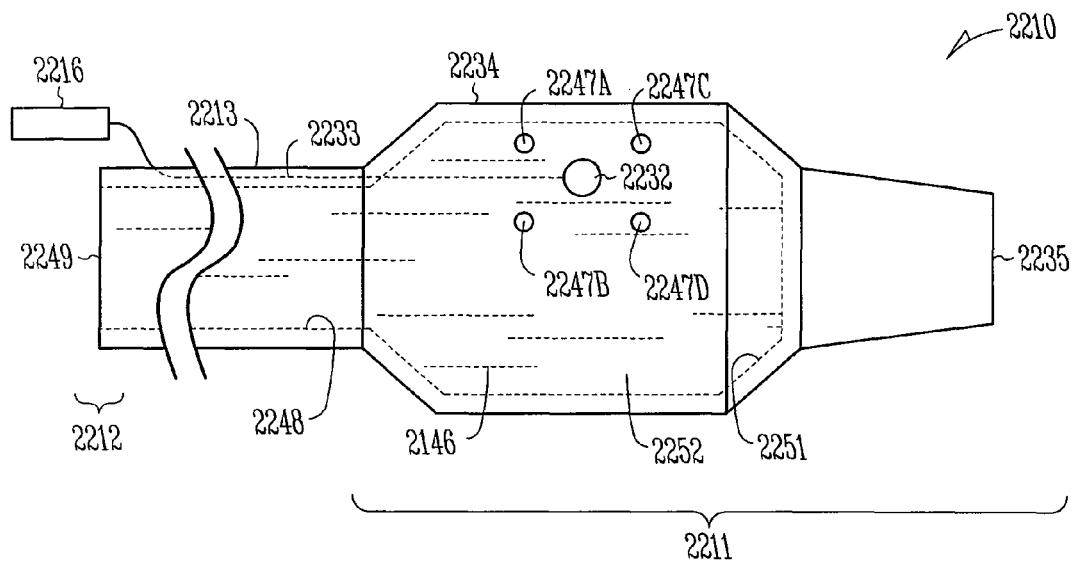
FIG. 22 is an illustration of another embodiment of a pacing catheter releasing conductive liquid.

FIGS. 21-23 illustrate various embodiments of a pacing catheter that includes a pacing electrode and releases a conductive liquid into a blood vessel to provide a conductive medium between a pacing electrode of the vascular wall of the blood vessel. This conductive medium increases electrical conductivity between the pacing electrode and the target tissue, thereby lowering the pacing energy required to capture the heart. In various embodiments, the conductive liquid has an electrical conductivity that is substantially higher than the electrical conductivity of blood.

FIG. 21 is an illustration of an embodiment of a pacing catheter 2110 (cross-sectional view), which releases a conductive liquid 2146, and an injection device 2150. Pacing catheter 2110 is a PTVI device including a proximal end portion 2112, a distal end portion 2111 configured for intravascular placement and including a distal tip 2135, an elongate shaft 2113 coupled between proximal end portion 2112 and distal end portion 2111, a lumen 2148 extending within shaft 2113, and exit ports 2147A-B. Lumen 2148 has a proximal opening 2149 at proximal end portion 2112 and connects to exit ports 2147A-B. Conductive liquid 2146 is injected into lumen 2148 from injection device 2150 through proximal opening 2149 and exits into a blood vessel from lumen 2148 through exit ports 2147A-B.

Pacing catheter 2110 includes a pacing electrode 2132 incorporated onto distal tip 2135, a connector 2116 at proximal end portion 2112, and a conductor 2133 providing for electrical connection between pacing electrode 2132 and connector 2116. After being released into the blood vessel, conductive liquid 2146 improves electrical conductivity between pacing electrode 2132 and the vascular wall, thereby reducing the impedance between the pair of anode and cathode through which pacing pulses are delivered. In one embodiment, conductive liquid 2146 includes saline. In one embodiment, conductive liquid 2146 is radiopaque. In one embodiment, conductive liquid 2146 includes saline and radiopaque contrast liquid, such as a mixture of approximately 50% of saline and 50% of the radiopaque contrast liquid.

In one embodiment, exit ports 2147A-B are configured to allow controllable release of conductive liquid 2146 into the blood vessel. In one embodiment, exit ports 2147A-B each include electrically activated polymer (EAP) functioning as a valve that is controlled by an electric field applied using electrode 2132. While one pacing electrode 2132 and two exit ports 2147A-B are shown in FIG. 21 for illustrative purposes, in various embodiments, pacing catheter 2110 includes any number of pacing electrode(s) and any number of exit port(s) arranged to release conductive liquid to increase the electrical conductivity between the pacing electrode(s) and the target tissue for pacing.

FIG. 22 is an illustration of an embodiment of a pacing catheter 2210 releasing conductive liquid 2146. Pacing catheter 2210 is a PTVI device including a proximal end portion 2212, a distal end portion 2211 configured for intravascular placement and including a distal tip 2235 and a drip balloon 2234, an elongate shaft 2213 coupled between proximal end portion 2212 and distal end portion 2211, a lumen 2248 extending within shaft 2213, and exit ports 2247A-D. Lumen 2248 has a proximal opening 2249 at proximal end portion 2212 and connects to exit ports 2247A-D. Conductive liquid 2146 is injected into lumen 2248 from injection device 2150 through proximal opening 2249 and exit into a blood vessel from lumen 2248 through exit ports 2147A-D.

Pacing catheter 2210 includes a pacing electrode 2232 incorporated onto drip balloon 2234, a connector 2216 at proximal end portion 2212, and a conductor 2233 providing for electrical connection between pacing electrode 2232 and connector 2216. Drip balloon 2234 includes a wall 2251 forming a chamber 2252 to contain conductive liquid 2146. Wall 2251 includes holes functioning as exit ports 2247A-D, which allow for dripping of conductive liquid 2146 from chamber 2252 to the blood vessel. In one embodiment, the holes are opened to allow for dripping of conductive liquid 2146 to the blood vessel when drip balloon 2234 is inflated. After being released into the blood vessel, conductive liquid 2146 improves electrical conductivity between pacing electrode 2232 and the vascular wall.

In one embodiment, injection device 2150 injects conductive liquid 2146 into chamber 2252 through lumen 2248 to inflate drip balloon 2234 and withdraws conductive liquid 2146 from chamber 2252 through lumen 2248 to deflate drip balloon 2234. This allows for delivering combined ischemic cardioprotection therapy by inflating and deflating drip balloon 2234 and pacing cardioprotection therapy by delivering cardioprotective pacing via pacing electrode 2232 and conductive liquid 2146.

While four exit ports 2247A-D are shown in FIG. 22 for illustrative purposes, pacing catheter 2210 includes any number of exit port(s). In one embodiment, pacing catheter 2210 allows for delivering combined ischemic cardioprotection therapy by inflating and deflating drip balloon 2234 and pacing cardioprotection therapy by delivering cardioprotective pacing via electrodes 2232 and conductive liquid 2146.

Figures 23A, 23B:
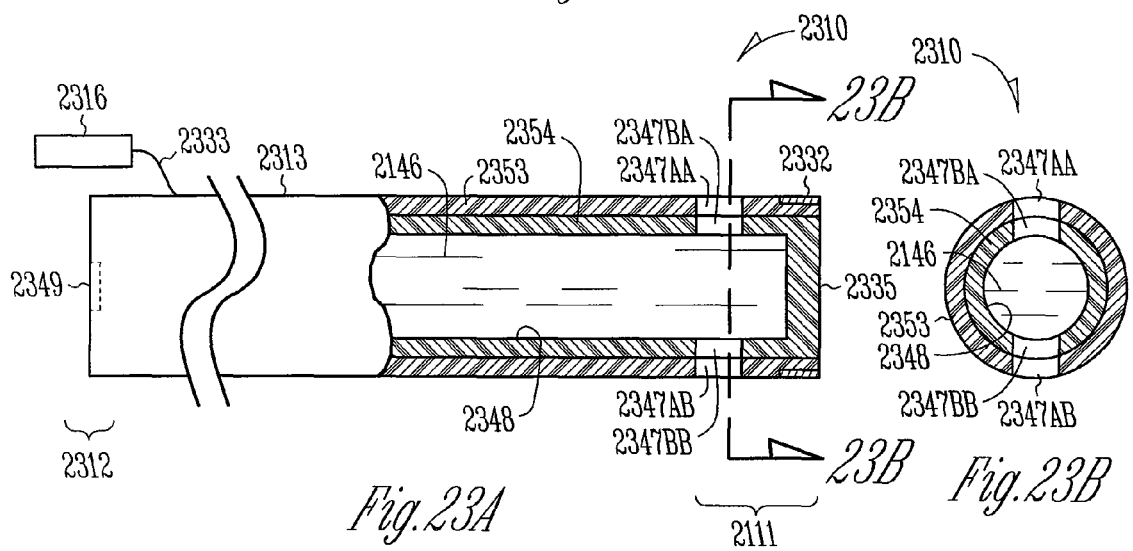
FIGS. 23A-B are an illustration of another embodiment of a pacing catheter releasing conductive liquid.

FIG. 23A is a side view, and FIG. 23B is a cross-sectional view, illustrating an embodiment of a pacing catheter 2310 releasing conductive liquid 2146. Pacing catheter 2310 is a PTVI device including a proximal end portion 2312, a distal end portion 2311 configured for intravascular placement and including a distal tip 2335, and an elongate shaft 2313 coupled between proximal end portion 2312 and distal end portion 2311. Pacing catheter 2310 includes an inner tube 2354 including a lumen 2348 and an outer tube 2353 accommodating at least a portion of inner tube 2354. Inner tube includes inner orifices 2347BA-B. Outer tube 2353 includes outer orifices 2347AA-B. The release of conductive liquid 2146 from lumen 2348 is controlled by rotating inner tube 2354 relative to outer tube 2353 to create an opening by aligning inner orifices 2347BA-B and outer orifices 2347AA-B. Lumen 2348 has a proximal opening 2349 at proximal end portion 2312 and connects inner orifices 2347BA-B. Conductive liquid 2146 is introduced into lumen 2348 from injection device 2150 through proximal opening 2349. When aligned, orifices 2347AA and 2347BA form an exit port, and orifices 2347BA and 2347BB form another exit port, to allow conductive liquid 2146 to flow from lumen 2348 to the blood vessel.

Pacing catheter 2310 includes a pacing electrode 2332 incorporated onto distal end portion 2311, a connector 2316 at proximal end portion 2312, and a conductor 2333 providing for electrical connection between pacing electrode 2332 and connector 2316. After being released into the blood vessel, conductive liquid 2146 improves electrical conductivity between pacing electrode 2332 and the vascular wall.

While two pairs of inner and outer orifices forming two exit ports are shown in FIG. 23 for illustrative purposes, pacing catheter 2310 includes any number of pairs of inner and outer orifices forming any number of exit ports.

Example: Pacemaker Integrated with PTVI Device

FIGS. 24-28 illustrate various embodiments of a pacemaker and pacing electrodes integrated with a PTVI device. Such an integrated pacemaker-PTVI device eliminates the need for connecting a separate pacemaker to a PTVI device, thereby simplifying the equipment setup for pacing during a revascularization procedure.

Figure 24:
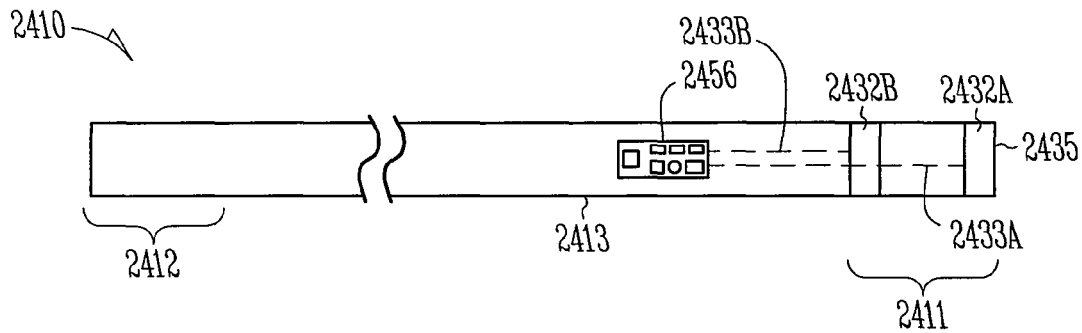
FIG. 24 is an illustration of an embodiment of a pacemaker integrated into a PTVI device.

FIG. 24 is an illustration of an embodiment of a pacemaker 2456 integrated with a PTVI device 2410. PTVI device 2410 includes a proximal end portion 2412, a distal end portion 2411 configured for intravascular placement and including a distal tip 2435, and an elongate shaft 2413 coupled between proximal end portion 2412 and distal end portion 2411. In the illustrated embodiment, pacemaker 2456 is incorporated onto shaft 2413. Pacing electrodes 2432A-B are incorporated onto distal end portion 2411 and electrically connected to pacemaker 2456 via conductors 2433A-B. In various embodiments, PTVI device 2410 includes any number of pacing electrodes incorporated onto one or more of distal end portion 2411 and shaft 2413. Examples of PTVI device 2410 include a guide wire, a guide catheter, and an angioplasty catheter. In various embodiments, pacemaker 2456 is integrated into any of the PTVI devices discussed in the document.

Figure 25:
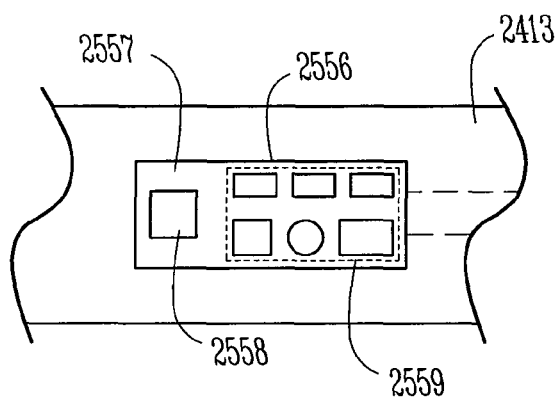
FIG. 25 is an illustration of an embodiment of the pacemaker of FIG. 24.

FIG. 25 is an illustration of an embodiment of a pacemaker 2556. Pacemaker 2556 is an embodiment of 2456 and includes a flexible pacemaker circuit including an electronic circuit 2559 and a battery 2558 both built on a flexible circuit substrate 2557. Flexible circuit substrate 2557 is affixed to PTVI device 2410. In one embodiment, electronic circuit 2559 includes a pacing output circuit such as pacing output circuit 224 and a control circuit such as control circuit 226. In one embodiment, battery 2558 is a solid state battery, such as a solid state lithium battery, deposited on flexible circuit substrate 2557. In one embodiment, battery 2558 is capable of providing electronic circuit 2559 with energy for delivering pacing pulses according to the cardioprotective pacing protocol for about 10 minutes.

In one embodiment, electronic circuit 2559 includes a control circuit that initiates the delivery of pacing pulses when pacing electrodes 2432A-B contact blood, such as when distal end portion 2411 exits from a guide catheter or other sheath. In another embodiment, electronic circuit 2559 is communicatively coupled to an external device via a wired or wireless communication link, and initiates the delivery of pacing pulses in response to a command received from the external device. In another embodiment, electronic circuit 2559 includes a switch that is mechanically controlled through a string, a sheath, or other mechanical link extending within or over PTVI device 2410. The switch allows initiation, suspension, and/or termination of the delivery of pacing pulses at proximal end portion 2412. In one embodiment, the duration of the delivery of pacing pulses is programmed into electronic circuit 2559. For example, the electronic circuit 2559 is programmed to execute the cardioprotective pacing protocol discussed above with reference to FIG. 3, and the delivery of the pacing pulses is terminated when the pacing sequence specified by the cardioprotective pacing protocol is completed. In circumstances of emergency, such as when fibrillation is detected, the delivery of pacing pulses is stopped by a command from the external device or the mechanically controlled switch, whichever is available, or by removing PTVI device 2410 from the patient.

Figure 26:
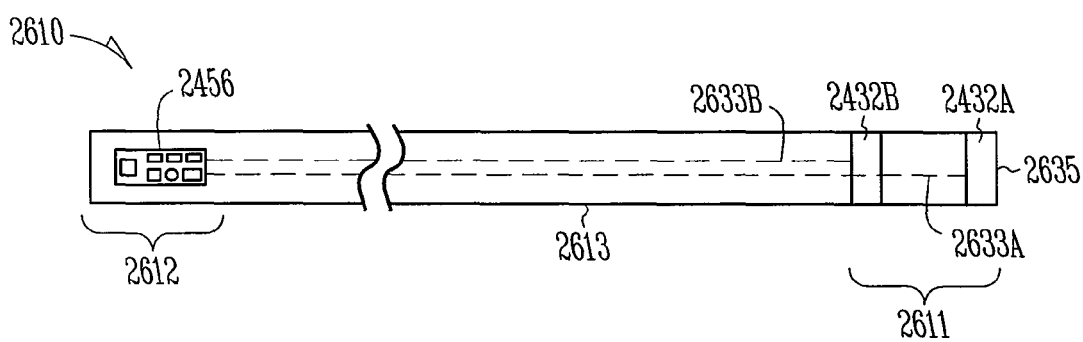
FIG. 26 is an illustration of another embodiment of a pacemaker integrated into a PTVI device.

FIG. 26 is an illustration of an embodiment of pacemaker 2456 integrated with a PTVI device 2610. PTVI device 2610 is another embodiment of PTVI device 2410 and includes a proximal end portion 2612, a distal end portion 2611 configured for intravascular placement and including a distal tip 2635, and an elongate shaft 2613 coupled between proximal end portion 2612 and distal end portion 2611. Pacemaker 2456 is incorporated onto proximal end portion 2612. Pacing electrodes 2432A-B are incorporated onto distal end portion 2611 and electrically connected to pacemaker 2456 via conductors 2633A-B.

Figure 27:
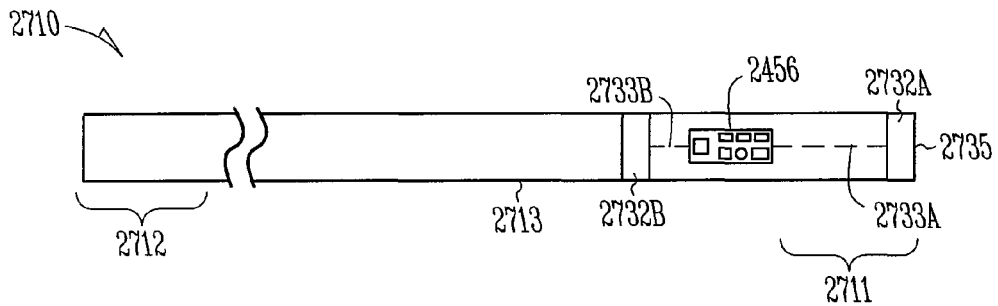
FIG. 27 is an illustration of another embodiment of a pacemaker integrated into a PTVI device.

FIG. 27 is an illustration of an embodiment of pacemaker 2456 integrated with a PTVI device 2710. PTVI device 2710 is another embodiment of PTVI device 2410 and includes a proximal end portion 2712, a distal end portion 2711 configured for intravascular placement and including a distal tip 2735, and an elongate shaft 2713 coupled between proximal end portion 2712 and distal end portion 2711. Pacemaker 2456 is incorporated onto shaft 2713. A pacing electrode 2732A is incorporated onto distal end portion 2711 and electrically connected to pacemaker 2456 via a conductor 2733A. Another pacing electrode 2732B is incorporated onto shaft 2713 and electrically connected to pacemaker 2456 via a conductor 2733B.

Figure 28:
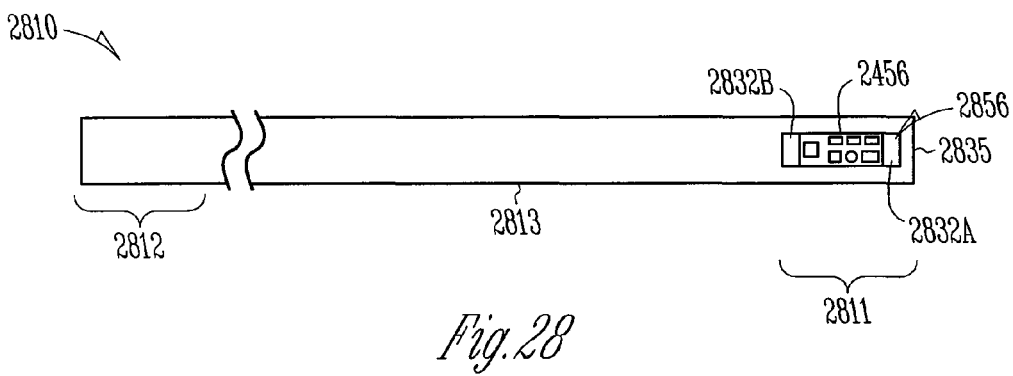
FIG. 28 is an illustration of another embodiment of a pacemaker integrated into a PTVI device.

FIG. 28 is an illustration of an embodiment of a pacemaker 2856 integrated into a PTVI device 2810. PTVI device 2810 is another embodiment of PTVI device 2410 and includes a proximal end portion 2812, a distal end portion 2811 configured for intravascular placement and including a distal tip 2835, and an elongate shaft 2813 coupled between proximal end portion 2812 and distal end portion 2811. Pacemaker 2856 includes a flexible pacemaker circuit including electronic circuit 2559, solid state battery 2558, and pacing electrodes 2832A-B, all of which built on flexible circuit substrate 2557. In other words, pacemaker 2856 includes pacemaker 2456 and pacing electrodes 2832A-B built on a flexible circuit substrate, where pacing electrodes 2832A-B are electrically connected to pacemaker 2456.

PTVI devices 2410, 2610, 2710, and 2810 are discussed above for illustrative purposes. In various embodiment, a pacemaker such as pacemaker 2456 or 2856 and two or more pacing electrodes are integrated into a PTVI device for delivering pacing pulses during a revascularization procedure. In various embodiments, the PTVI device with which the pacemaker is integrated includes any PTVI device discussed in this document. In one embodiment, such a PTVI device including built-in pacemaker and pacing electrodes are constructed as a disposable device for a single use.

Example: Angioplasty Catheter with Pacing Electrodes on Shaft

FIGS. 29-33 illustrate various examples of one or more pacing electrodes incorporated onto the shaft of an angioplasty catheter such as a balloon catheter. In its expanded state, such as when a balloon is inflated, the angioplasty device at the distal end portion of the angioplasty catheter functions as an anchor to stabilize the location of the pacing electrode(s) in a blood vessel. In one embodiment, the one or more pacing electrodes are displaceable along the shaft of the angioplasty catheter. This allows, for example, the pacing site(s) to be positioned upstream and away from the infarcted region, thereby lowering the energy required to capture the heart by delivering pacing pulses to normal tissue, which is known to be less conductive than infarct tissue. In another embodiment, the angioplasty catheter includes an outer shell made of conductive material, and at least a portion of the outer shell functions as a pacing electrode.

Figure 29:
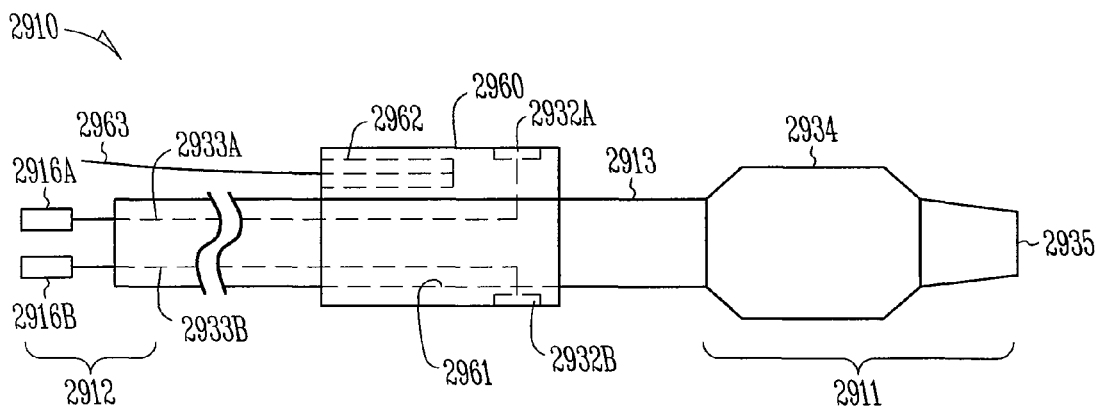
FIG. 29 is an illustration of an embodiment of an angioplasty catheter including pacing electrodes on the shaft.

FIG. 29 is an illustration of an embodiment of an angioplasty catheter 2910. Angioplasty catheter 2910 is a PTVI device that includes a proximal end portion 2912, a distal end portion 2911 configured for intravascular placement and including an angioplasty device 2934 and a distal tip 2935, and an elongate shaft 2913 coupled between proximal end portion 2912 and distal end portion 2911. In the illustrated embodiment, a sleeve 2960 is placed over shaft 2913. Pacing electrodes 2932A-B are incorporated onto sleeve 2960 and electrically connected to connectors 2916A-B at proximal end portion 2912 via conductors 2933A-B. Sleeve 2960 includes a first lumen 2961 and a second lumen 2962. Lumen 2961 is configured to accommodate a portion of shaft 2913 and allow sleeve 2960 with electrodes 2932A-B to slide over shaft 2913. Conductors 2933A-B each have an adjustable length, displaceable along shaft 2913, or otherwise flexible to allow the displacement of sleeve 2960 over shaft 2913. Lumen 2962 is configured to receive a push wire 2963 for moving sleeve 2960 along shaft 2913.

In one embodiment, angioplasty device 2934 includes a balloon. When inflated, balloon 2934 functions as an anchor to stabilize the locations of pacing electrodes 2932A-B. For example, after expanding balloon 2934, electrodes 2932A-B are positioned by sliding sleeve 2960 along shaft 2913. In various embodiments, angioplasty catheter 2910 includes one or more sleeves over shaft 2913. Each sleeve includes one or more pacing electrodes.

Figure 30:
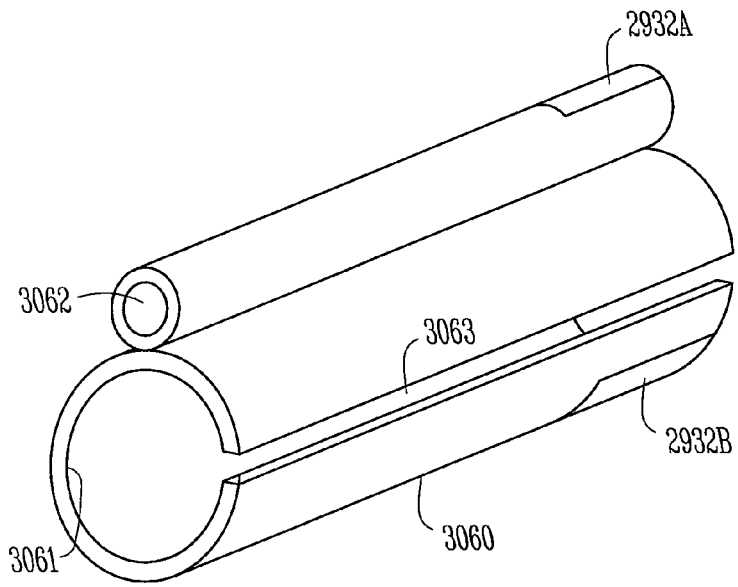
FIG. 30 is an illustration of an embodiment of a sleeve of the angioplasty catheter of FIG. 29.

FIG. 30 is an illustration of an embodiment of a sleeve 3060, which is an embodiment of sleeve 2960 and is configured to be placed over shaft 2913. Sleeve 3060 is a flexible C-shaped sleeve including a slit 3063, a first lumen 3061, a second lumen 3062, and pacing electrodes 2932A-B. Slit 3063 extends longitudinally along sleeve 3060 to allow sleeve 3060 to be pushed onto shaft 2913 and peeled away from shaft 2913. Lumen 3061 is configured to accommodate a portion of shaft 2913 and allow sleeve 3060 to slide along a portion of shaft 2913. Lumen 3062 is configured to receive a push wire allowing sleeve 3060 to be pushed to slide along shaft 2913.

Figure 31:
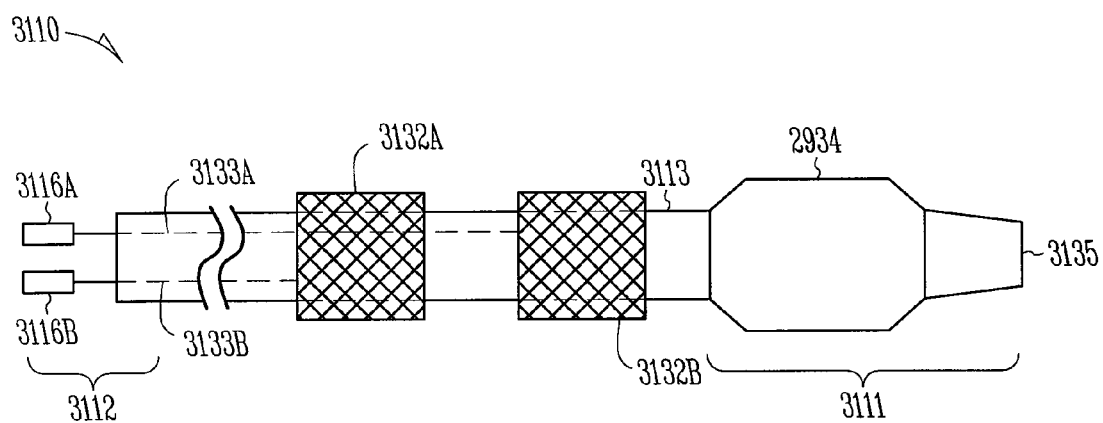
FIG. 31 is an illustration of another embodiment of an angioplasty catheter including pacing electrodes on the shaft.

FIG. 31 is an illustration of an embodiment of an angioplasty catheter 3110, which is another embodiment of angioplasty catheter 2910. Angioplasty catheter 3110 is a PTVI device that includes a proximal end portion 3112, a distal end portion 3111 configured for intravascular placement and including angioplasty device 2934 and a distal tip 3135, and an elongate shaft 3113 coupled between proximal end portion 3112 and distal end portion 3111. In the illustrated embodiment, pacing electrodes 3132A-B, each configured as a stent, are placed over shaft 3113 and electrically connected to connectors 3116A-B at proximal end portion 3112 via conductors 3133A-B. In one embodiment, pacing electrodes 3132A-B are each configured as a flexible stent. In one embodiment, conductors 3133A-B each have an adjustable length, displaceable along shaft 3113, or otherwise flexible to allow the displacement of pacing electrodes 3132A-B over shaft 3113. In various embodiments, angioplasty catheter 3110 includes one or more pacing electrodes configured as one or more stents over shaft 3113.

Figure 32:
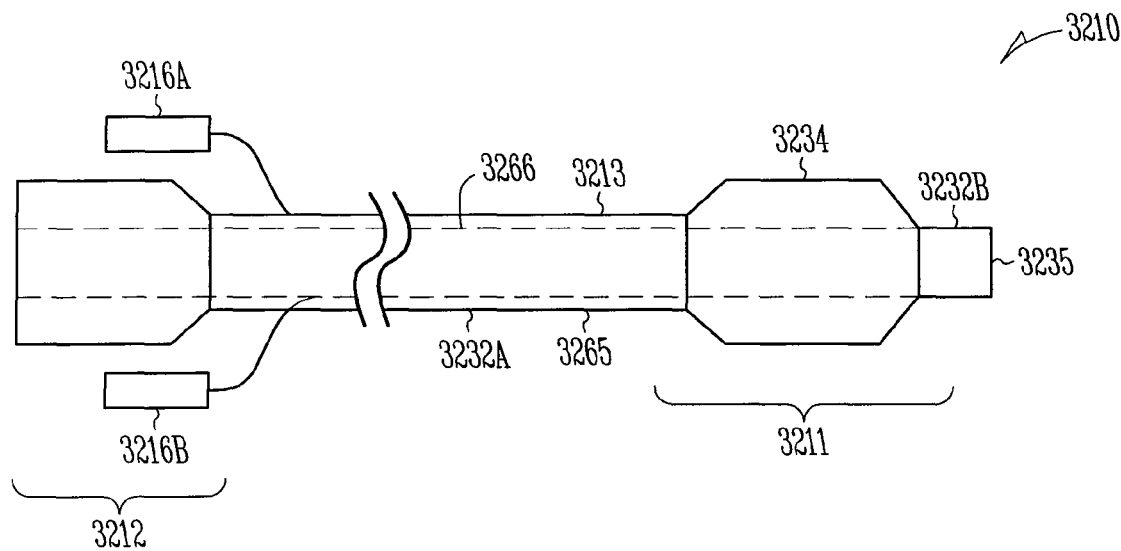
FIG. 32 is an illustration of another embodiment of an angioplasty catheter including pacing electrodes on the shaft.

FIG. 32 is an illustration of an embodiment of an angioplasty catheter 3210. Angioplasty catheter 3210 is a PTVI device that includes a proximal end portion 3212, a distal end portion 3211 configured for intravascular placement and including an angioplasty device 3234 and a distal tip 3235, and an elongate shaft 3213 coupled between proximal end portion 3212 and distal end portion 3211. In the illustrated embodiment, shaft 3213 includes an outer shell 3265 that includes a conductive portion functioning as a pacing electrode 3232A. Pacing electrode 3232A is electrically connected to a connector 3216A at proximal end portion 3212. In one embodiment, outer shell 3265 includes a flexible metal tube. In one embodiment, pacing electrode 3232A includes approximately the entire outer shell 3265, or a substantial portion of outer shell 3265. In the illustrated embodiment, angioplasty catheter 3210 also includes an elongate conductive inner portion 3266 extending through approximately the enough length of angioplasty catheter 3310. Inner portion 3266 includes an exposed conductive distal end functioning as another pacing electrode 3232B. Pacing electrode 3232B is electrically connected to a connector 3216B at proximal end portion 3212. In one embodiment, inner portion 3266 is a flexible metal wire. In another embodiment, inner portion 3266 is a flexible metal tube. In one embodiment, angioplasty device 3234 includes a balloon. Inner portion 3266 is a flexible metal tube with a lumen that allows for inflation and deflation of balloon 3234. When inflated, balloon 3234 functions as an anchor to stabilize the location of pacing electrodes 3232A-B. For example, after expanding balloon 3234, electrodes 3232A-B are positioned by sliding sleeve 3260 along shaft 3213.

Figure 33:
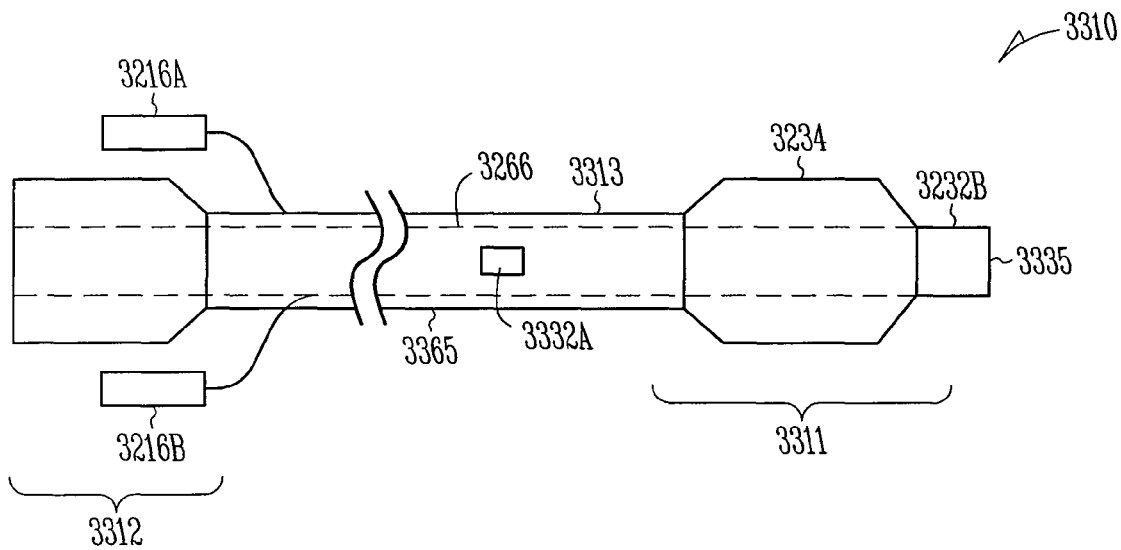
FIG. 33 is an illustration of another embodiment of an angioplasty catheter including pacing electrodes on the shaft.

FIG. 33 is an illustration of an embodiment of an angioplasty catheter 3310, which is another embodiment of angioplasty device 3210. Angioplasty catheter 3310 is a PTVI device that includes a proximal end portion 3312, a distal end portion 3311 configured for intravascular placement and including an angioplasty device 3234 and a distal tip 3335, and an elongate shaft 3313 coupled between proximal end portion 3312 and distal end portion 3311. Angioplasty catheter 3310 differs from angioplasty catheter 3210 in that shaft 3313 includes an outer shell 3365 that is coated with an insulation material to leave one or more exposed areas functioning as one or more pacing electrodes. In the illustrated embodiment, outer shell 3365 is coated with the insulation material to leave an exposed area functioning as a pacing electrode 3332A, which is electrically connected to connector 3216A at proximal end portion 3312.

In various embodiments, angioplasty catheters 2910, 3110, 3210, and 3310 each allow one or more pacing electrodes to be positioned by moving along and within a blood vessel after an expandable angioplasty device such as a balloon is expanded to function as an anchor. In one application, the one or more pacing electrodes are placed according to the pacing energy required, such as by locating the pacing site(s) associated with approximately minimum amplitude or width of the pacing pulses. In various embodiments, angioplasty catheters 2910, 3110, 3210, and 3310 each allow for delivering combined ischemic cardioprotection therapy by inflating and deflating a balloon of the catheter and pacing cardioprotection therapy by delivering cardioprotective pacing via one or more of the pacing electrodes of the catheter.

Example: Pacing Catheter with Stent Electrode

FIGS. 34-37 illustrate various examples of pacing electrode constructed as a stent or incorporated onto a stent. The stent is connected to a PTVI catheter. After being used for delivering pacing pulses during a revascularization procedure, the stent is disconnected from the PTVI catheter to stay in the patient, or removed from the patient with the PTVI catheter. In various embodiments, the pacing pulses are delivered when the stent is in its expanded state in a blood vessel for a stable electrical contact between the pacing electrode and the vascular wall of the blood vessel.

Figure 34:
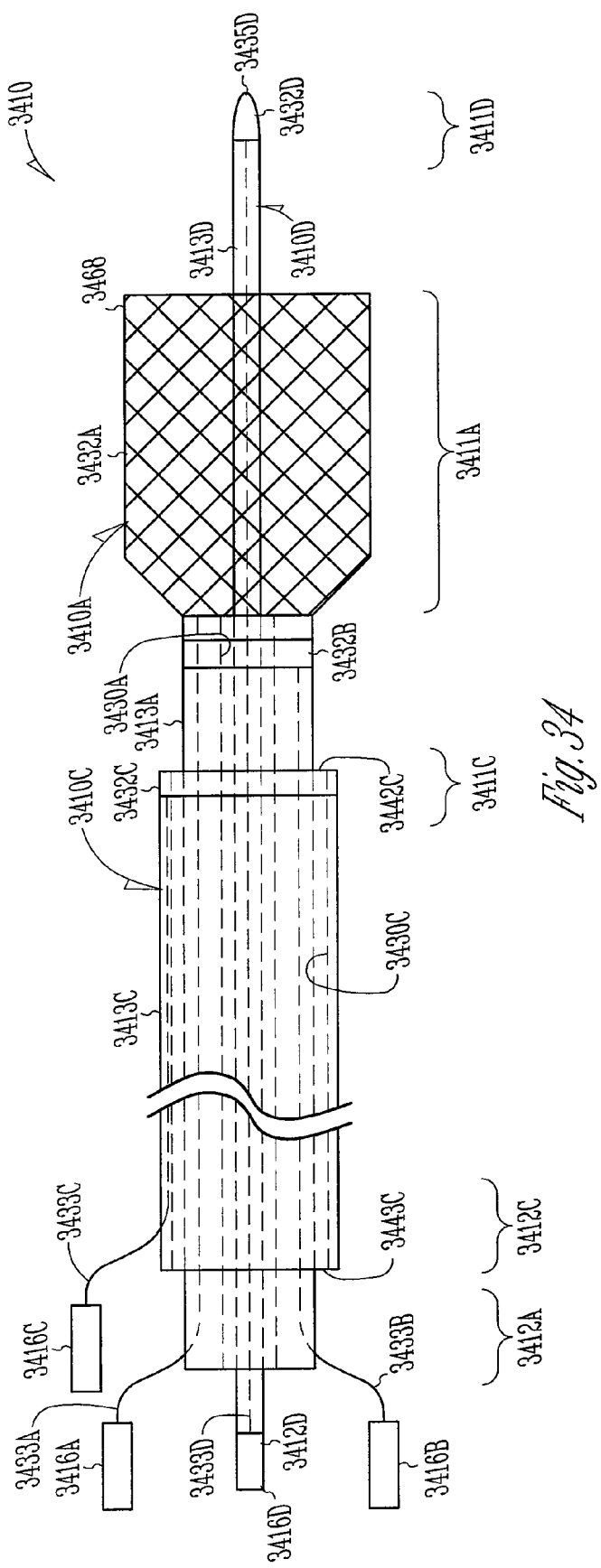
FIG. 34 is an illustration of an embodiment of a pacing catheter assembly including a stent catheter with a stent electrode.

FIG. 34 is an illustration of an embodiment of a pacing catheter 3410. Pacing catheter 3410 is a PTVI device assembly including a stent catheter 3410A, a sheath 3410C, and a guide wire 3410D.

Stent catheter 3410A includes a catheter proximal end portion 3412A, a catheter distal end portion 3411A configured for intravascular placement and including a stent 3468, an elongate catheter shaft 3413A coupled between proximal end portion 3412A and distal end portion 3411A, and a catheter lumen 3430A extending within shaft 3413A between proximal end portion 3412A and distal end portion 3411A. Stent 3468 includes a pacing electrode 3432A. A conductor 3433A electrically connects pacing electrode 3432A to a connector 3416A at proximal end portion 3412A. In the illustrated embodiment, another pacing electrode 3432B is incorporated onto shaft 3413A. Another conductor 3433B electrically connects pacing electrode 3432B to a connector 3416B at proximal end portion 3412A.

Sheath 3410C includes a sheath proximal end portion 3412C, a sheath distal end portion 3411C configured for intravascular placement, an elongate sheath shaft 3413C coupled between proximal end portion 3412C and distal end portion 3411C, and a sheath lumen 3430C extending within shaft 3413C between proximal end portion 3412C and distal end portion 3411C. Lumen 3430C has a diameter accommodating a portion of stent catheter 3410A, including shaft 3413A and stent 3468 in its restrained state. Lumen 3430C has a proximal opening 3443C at distal end portion 3412C and a distal opening 3442C at distal end portion 3411C. In one embodiment, sheath 3410C is a guide catheter used in a revascularization procedure. In the illustrated embodiment, a pacing electrode 3432C is incorporated onto distal end portion 3411C. A conductor 3433C electrically connects pacing electrode 3432C to a connector 3416C at proximal end portion 3412C.

Guide wire 3410D includes a guide wire proximal end portion 3412D, a guide wire distal end portion 3411D including a guide wire distal tip 3435D, and an elongate guide wire shaft 3413D coupled between proximal end portion 3412D and distal end portion 3411D. In the illustrated embodiment, a pacing electrode 3432D is incorporated onto distal tip 3435D. A conductor 3433D electrically connects pacing electrode 3432D to a connector 3416D at proximal end portion 3412D.

In one embodiment, stent catheter 3410A is a stent delivery catheter, and stent 3468 is detachably connected to shaft 3413A to be permanently implanted in a blood vessel after the pacing pulses are delivered during the revascularization procedure. In another embodiment, stent catheter 3410A is dedicated for pacing during the revascularization procedure, and stent 3468 is non-detachably connected to shaft 3413A to be removed from the blood vessel after the pacing therapy is completed.

In one embodiment, stent 3468 includes metal mesh functioning as pacing electrode 3432A. In another embodiment, pacing electrode 3432A is an electrode attached onto the mesh of stent 3468.

In various embodiments, stent 3468 is expandable and contractible by pushing and pulling sheath 3410C and/or stent catheter 3410A. Stent 3468 exits from lumen 3430C through distal opening 3442C by pulling sheath 3410C toward the proximal direction (away from the patient) and/or pushing stent catheter 3410A toward the distal direction (toward the patient). In one embodiment, stent 3468 is self-expandable upon exiting from sheath 3410C through distal opening 3442C. Stent 3468 is also retractable into lumen 3430C through distal opening 3442C by pushing sheath 3410C toward the distal direction (toward the patient) and/or pulling stent catheter 3410A toward the proximal direction (away from the patient).

In various embodiments, pacing catheter 3410 includes pacing electrode 3432A and one or more of pacing electrodes 3432B-D. In one embodiment, as illustrated in FIGS. 35 and 36 below, stent 3468 includes two pacing electrodes, and pacing electrodes 3432B-D are optional.

Figure 35:
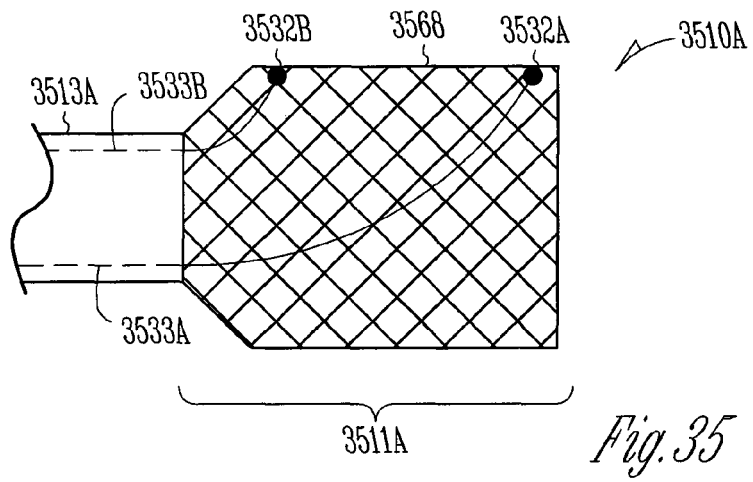
FIG. 35 is an illustration of an embodiment of the distal end portion of the stent catheter of FIG. 34.

FIG. 35 is an illustration of an embodiment of a distal end portion 3511A of a stent catheter 3510A, which is another embodiment of stent catheter 3410A. Distal end portion 3511A includes a stent 3568. Pacing electrodes 3532A-B are each affixed onto the mesh of stent 3568 and connected to one of conductors 3533A-B extending through a catheter shaft 3513A.

Figure 36:
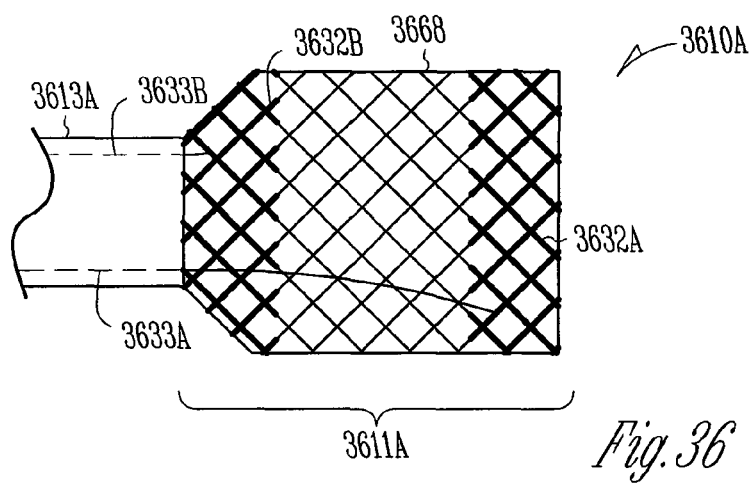
FIG. 36 is an illustration of another embodiment of the distal end portion of the stent catheter of FIG. 34.

FIG. 36 is illustration of an embodiment of a distal end portion 3611A of a stent catheter 3610A, which is another embodiment of stent catheter 3410A. Distal end portion 3611A includes a stent 3668. Pacing electrodes 3632A-B each include a portion of the mesh of stent 3668 and connected to one of conductors 3633A-B extending through a catheter shaft 3613A. The two mesh portions forming pacing electrodes 3632A-B are electrically insulated from each other.

Figure 37:
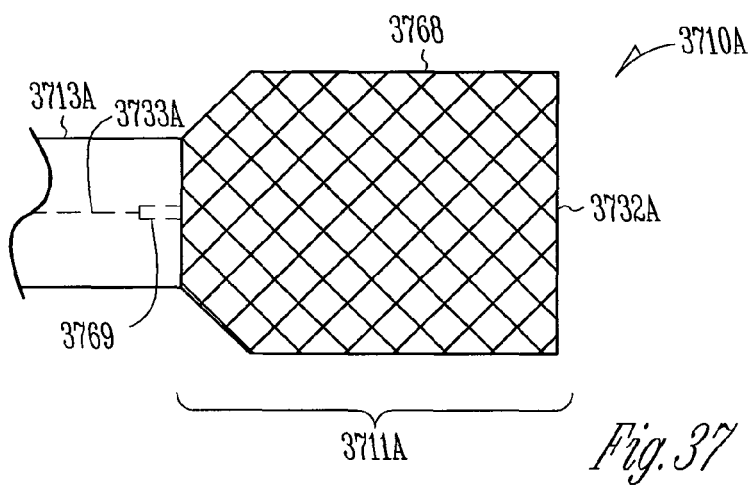
FIG. 37 is an illustration of another embodiment of the distal end portion of the stent catheter of FIG. 34.

FIG. 37 is an illustration of an embodiment of a distal end portion 3711A of a stent catheter 3710A, which is another embodiment of stent catheter 3410A. Distal end portion 3711A includes a stent 3768 detachably connected to a catheter shaft 3713A through a connector 3769. Stent 3768 is capable of functioning as a pacing electrode 3732A when being connected to shaft 3713A through connector 3769, which also provides electrical connection between pacing electrode 3732A and a conductor 3733A extending through shaft 3713A. Connector 3769 is dissolvable by electrolysis when exposed to the blood. In one embodiment, connector 3769 is dissolved by applying an electrical current through it while being exposed to the blood. This allows stent 3768 to be disconnected from shaft 3713A and stay in the blood vessel after the pacing pulses are delivered during the revascularization procedure.

It is to be understood that the above detailed description, including the various examples of PTVI devices and external pacemakers, is intended to be illustrative, and not restrictive. In general, cardioprotective pacing is applied to prevent or reduce cardiac injury associated with ischemia by using one or more pacing electrodes incorporated onto any intravascular device and a pacemaker that is capable of delivering pacing pulses by executing a cardioprotective pacing protocol. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A percutaneous transluminal vascular intervention (PTVI) device assembly for use during revascularization of a blood vessel, the PTVI device assembly comprising:
   a plurality of pacing leads each including a pacing lead distal end portion and one or more pacing electrodes incorporated onto the pacing lead distal end portion;
   a catheter including:
      a catheter proximal end portion;
      a catheter distal end portion configured to be placed in the blood vessel and including a catheter distal tip;
      an elongate catheter shaft coupled between the catheter proximal end portion and the catheter distal end portion;
      one or more entry ports at the catheter proximal end portion;
      a plurality of exit ports including at least one exit port at the catheter distal tip; and
      a further pacing electrode at the catheter distal tip,
      the catheter configured to allow the pacing lead distal end portion of each pacing lead of the plurality of pacing leads to enter an entry port of the one or more entry ports and exit from an exit port of the plurality of exit ports; and
   a pacemaker configured to be connected to the pacing lead distal end portions of the plurality of pacing leads, the pacemaker including:
      a pacing output circuit configured to deliver pacing pulses through the one or more pacing electrodes and the further pacing electrode; and
      a control circuit coupled to the pacing output circuit and configured to execute a cardioprotective pacing protocol specifying one or more cardiac protection pacing sequences each including alternating pacing and non-pacing periods, the pacing periods each having a pacing duration during which a plurality of the pacing pulses is timed to be delivered according to a stress augmentation pacing mode to augment myocardial mechanical stress to a level effecting cardioprotection against myocardial injury, the non-pacing periods each having a non-pacing duration during which none of the pacing pulses is timed to be delivered.

2. The PTVI device assembly of claim 1, wherein the pacing leads each comprise:
   a pacing lead proximal end portion; and
   an elongate pacing lead shaft coupled between the pacing lead proximal end portion and the pacing lead distal end portion.

3. The PTVI device assembly of claim 1, wherein the catheter shaft comprises an exit port of the plurality of exit ports.

4. The PTVI device assembly of claim 1, wherein the catheter comprises a plurality of guiding channels each including a lumen extending within a portion of the catheter shaft and including a proximal opening at an entry port of the one or more entry ports and a distal opening at an exit port of the plurality of exit ports, the guiding channels each configured to allow the pacing lead distal end portion of the each pacing lead of the plurality of pacing leads to pass through.

5. The PTVI device assembly of claim 4, wherein the exit ports are arranged to allow the distal end portions of the pacing leads to enter the blood vessel and one or more blood vessels branching from the blood vessel.

6. The PTVI device assembly of claim 1, wherein the plurality of pacing leads comprises two pacing leads.

7. The PTVI device assembly of claim 1, wherein the plurality of pacing leads comprises more than two pacing leads.

8. The PTVI device assembly of claim 1, wherein the pacing leads each comprise a plurality of pacing electrodes incorporated onto the pacing lead distal end portion.

9. The PTVI device assembly of claim 1, wherein the pacemaker further comprises:
   a chassis housing the pacing output circuit and the control circuit; and
   a user interface incorporated onto the chassis, the user interface configured to allow control of the delivery of the pacing pulses by a user.

10. The PTVI device assembly of claim 1, wherein the control circuit is configured to apply rapid, asynchronous pacing during each of the pacing periods.

11. The PTVI device assembly of claim 1, wherein the control circuit is configured to cause delivery of the pacing pulses at a rate substantially higher than an intrinsic heart rate during each of the pacing periods.

12. The PTVI device assembly of claim 11, wherein the stress augmentation pacing mode is a bradycardia pacing mode.

13. The PTVI device assembly of claim 11, wherein the stress augmentation pacing mode is an asynchronous pacing mode.

14. The PTVI device assembly of claim 1, wherein the one or more cardiac protection pacing sequences each include approximately 1 to 4 cycles of the alternating pacing and non-pacing periods.

15. The PTVI device assembly of claim 14, wherein the pacing periods are each in a range of approximately 30 seconds to 20 minutes, and the non-pacing periods are each in a range of approximately 30 seconds to 20 minutes.

16. The PTVI device assembly of claim 15, wherein the one or more cardiac protection pacing sequences each include 3 cycles of the alternating pacing and non-pacing periods, the pacing periods are each approximately 5 minutes, and the non-pacing periods are each approximately 5 minutes.

17. The PTVI device assembly of claim 14, wherein the pacing periods are each in a range of approximately 10 seconds to one minute, and the non-pacing periods are each in a range of approximately 10 seconds to one minute.

18. The PTVI device assembly of claim 17, wherein the one or more cardiac protection pacing sequences each include approximately 2 to 4 cycles of the alternating pacing and non-pacing periods, the pacing periods are each approximately 30 seconds, and the non-pacing periods are each approximately 30 seconds.

19. The PTVI device assembly of claim 1, further comprising a pacing protocol module configured to be detachably connected to the pacemaker, the pacing protocol module storing the cardioprotective pacing protocol.

20. The PTVI device assembly of claim 19, wherein the cardioprotective pacing protocol specifies the stress augmentation pacing mode with pacing parameters including an atrioventricular delay selected to augment the myocardial mechanical stress to the level effecting cardioprotection against myocardial injury.

* * * * *